United States Patent
Wildenhaus et al.

(10) Patent No.: US 12,431,234 B2
(45) Date of Patent: Sep. 30, 2025

(54) ENFORCED CONTENT INTERACTION TIMING FOR LIFESTYLE AND HEALTH RELATED BEHAVIOR CHANGE

(71) Applicant: McNeil AB, Helsingborg (SE)

(72) Inventors: Kevin J. Wildenhaus, Plymouth, MI (US); Sophie Edgar, Hoboken, NJ (US); Justin Mellinger, Philadelphia, PA (US); Ming Dong, Furlong, PA (US); Desislava Ivanova, Cambridge, MA (US); Danielle Giuseffi, Rapid City, SD (US)

(73) Assignee: McNeil AB, Helsingborg (SE)

( * ) Notice: Subject to any disclaimer, the term of this patent is extended or adjusted under 35 U.S.C. 154(b) by 41 days.

(21) Appl. No.: 17/556,654

(22) Filed: Dec. 20, 2021

(65) Prior Publication Data

US 2022/0199225 A1    Jun. 23, 2022

Related U.S. Application Data

(60) Provisional application No. 63/129,351, filed on Dec. 22, 2020.

(51) Int. Cl.
  *G16H 20/70* (2018.01)
  *G06F 3/04847* (2022.01)
  *G16H 20/60* (2018.01)

(52) U.S. Cl.
  CPC ......... *G16H 20/70* (2018.01); *G06F 3/04847* (2013.01); *G16H 20/60* (2018.01)

(58) Field of Classification Search
  CPC ....... G16H 20/70; G16H 20/60; G06F 3/0483

(Continued)

(56) References Cited

U.S. PATENT DOCUMENTS

| 5,596,994 A * | 1/1997 | Bro .............. H04M 3/465 600/545 |
| 2003/0027116 A1* | 2/2003 | O'Donnell ......... G06Q 30/0207 434/236 |

(Continued)

FOREIGN PATENT DOCUMENTS

WO    WO-2022086454 A1 *    4/2022   ........... A61B 5/0077

OTHER PUBLICATIONS

Pbert, et al., "Feasibility of a Smartphone App with Mindfulness Training for Adolescent Smoking Cessation", Springer Science Business Media, LLC, 2020, 14 pages.

*Primary Examiner* — Hiep V Nguyen
(74) *Attorney, Agent, or Firm* — Condo Roccia Koptiw LLP

(57) ABSTRACT

A computing device may be configured for user interaction with specific timing mechanisms and access rules that may improve a user's preparedness for and ultimate success with a behavior change effort, such as smoking cessation, healthy eating, and/or behaviors to promote a healthy pregnancy. The computing device may include a processor that executes an enforcement module on the condition that both a user attempts to access a first content-interaction module between the first end time on a first scheduled date and a second start time on a second scheduled date and the user did not attempt to access the first content-interaction module between the first start time on the first scheduled date and the first end time on the first scheduled date. The enforcement module may indicate that the first content-interaction module is no longer available and that a second content-interaction module will become available on the second scheduled date.

20 Claims, 19 Drawing Sheets

(58) Field of Classification Search
USPC .......................................................... 705/3
See application file for complete search history.

(56) References Cited

U.S. PATENT DOCUMENTS

2018/0075219 A1    3/2018  Klein et al.
2021/0084451 A1*  3/2021  Williams ................ H04W 4/38
2021/0319887 A1* 10/2021  Derrick, Jr. .......... A61B 5/7275

* cited by examiner

FIG. 4A FIG. 4B FIG. 4C FIG. 4D

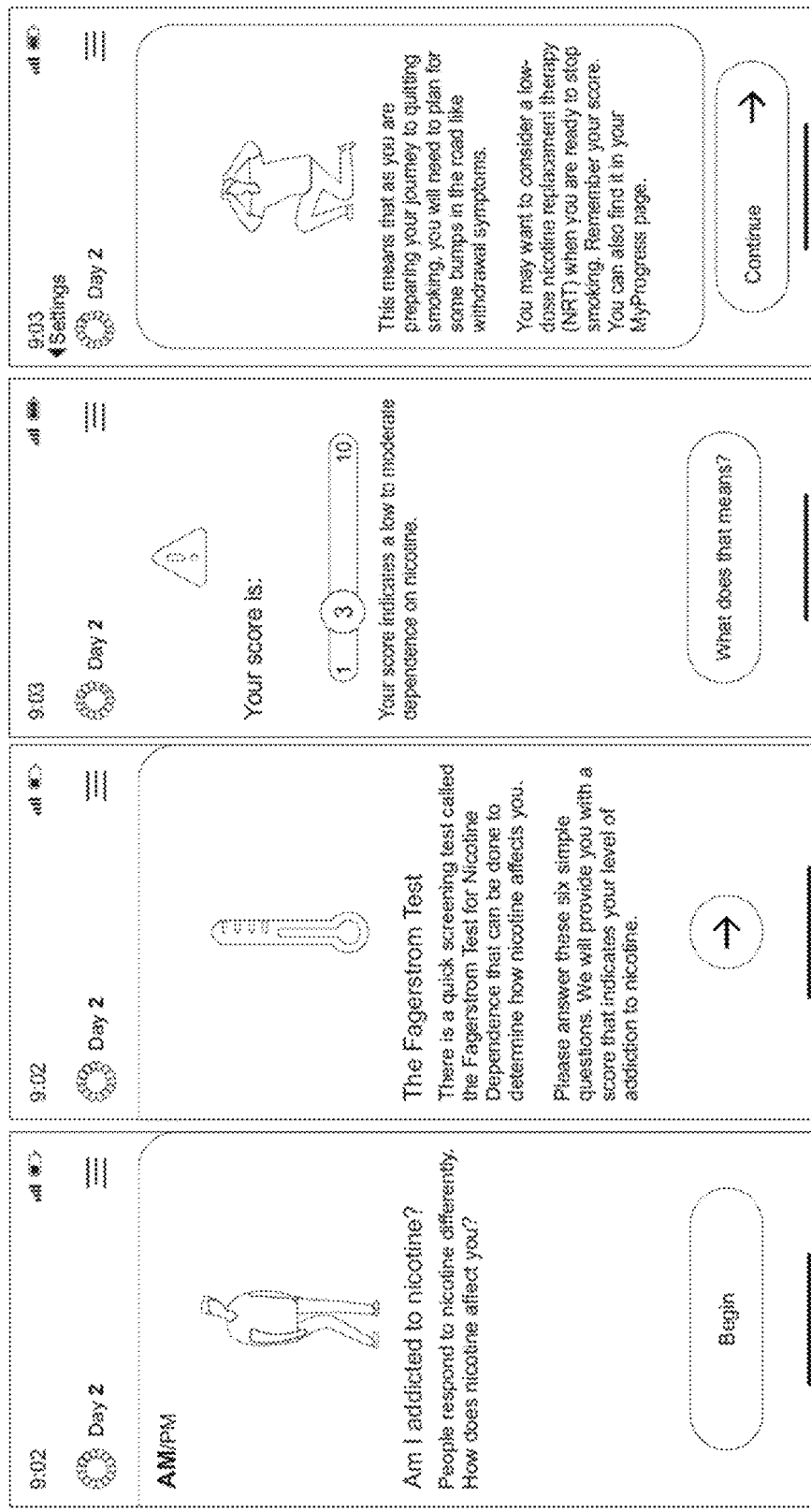

9:00

Welcome to Healthy Eating Skill Building. Before we get started, here are a few basic ground rules or things you should know.

NOTE: When we use the term "eat" we mean any food that we consume, both food we eat/chew and liquids that we drink.

Begin

ACTION STEP #1.
You want to eat healthier, which we think is an important decision. Let's start with a simple but very important question: *Why?*

*Why do I want to eat healthier?* Write in your reasons in the box below.

Enter Text

Done

Quick Tip Summary.

With your plan in place, get started on your assignments. Keep track of every food decision you make for the next 24 hours and tell at least 2 people listed above about your commitment. We will talk with you again in 2 days.

When you get our email, log in for Step #3.

Okay

Welcome back!

How did you do?

○ Kept track of food decisions.

○ Told at least 2 people about your commitment.

Next

FIG. 12D

ENFORCED CONTENT INTERACTION TIMING FOR LIFESTYLE AND HEALTH RELATED BEHAVIOR CHANGE

CROSS-REFERENCE TO RELATED APPLICATIONS

This application claims the benefit of U.S. Provisional Application No. 63/129,351, filed Dec. 22, 2020, the contents of which are incorporated by reference in their entirety herein.

BACKGROUND

The Transtheoretical Model (TTM) provides a conceptual framework for considering how individuals will move through sequential stages of behavior change. This model has been applied to a broad range of lifestyle and health related behaviors, including stress, depression, nutrition, physical activity, medication adherence, chronic disease self-management, and preventive medicine.

For example, TTM has most notably been studied with regard to smoking and efforts at cessation. Cigarette smoking continues to be one of the main risk factors for many chronic illnesses including cancer, lung diseases, and cardiovascular diseases. Current smokers fall within a wide spectrum of TTM stages ranging from precontemplation (e.g., not interested in quitting smoking in next 6 months); to contemplation (e.g., interested in quitting smoking in next 6 months but not next 30 days); to preparation (e.g., interested in quitting smoking in next 30 days). The majority of the current smokers are in the precontemplation and contemplation stages.

Technology-based solutions relating to lifestyle and health behavior changes, such as mobile apps for health behavior change, are often designed to provide full access to a comprehensive, longitudinal program, often without a clear end date. Further, they tend to make significant daily and longitudinal time demands, creating high user burden, and hence reducing sustained engagement. And technology-based solutions relating to smoking cessation, in particular, (e.g., smoking cessation mobile apps) generally do not target smokers in the precontemplation and contemplation stages. Rather, smoking cessation apps tend to be designed with an end goal of the smokers quitting while using the app and then following them for a period of time after the quit attempt in an effort to maintain quit status. Often, such apps fail to keep the smokers engaged throughout this process, and, as a result, see high dropout and early-abandonment rates.

SUMMARY

A computing device may be configured for user interaction with specific timing mechanisms and access rules that may improve a user's preparedness for and ultimate success with a behavior change effort. For example, the specific timing mechanisms and access rules may increase a user's motivation, confidence and/or readiness to make the behavior change effort. For example, the behavior change effort may relate to behaviors such as smoking cessation (e.g., a quit-smoking attempt), healthy eating, and/or behaviors to promote a healthy pregnancy. The computing device may include a processor that executes an enforcement module. The enforcement module may be associated with a first content-interaction module. The first content-interaction module may transition from an inactive state to an active state at a first start time on a first scheduled date. The first content-interaction module may be configured to present a user-activity content in the active state. The first content-interaction module may transition from the active state to the inactive state at a first end time on the first scheduled date. The first content-interaction module may restrict access to the user-activity content in the inactive state.

The enforcement module may execute on the condition that both a user attempts to access the first content-interaction module between the first end time on a first scheduled date and a second start time on a second scheduled date and the user did not attempt to access the first content-interaction module between the first start time on the first scheduled date and the first end time on the first scheduled date. The enforcement module may indicate that the first content-interaction module is no longer available and that a second content-interaction module will become available on the second scheduled date.

BRIEF DESCRIPTION OF THE DRAWINGS

FIGS. 4A-J are mobile application user interface (UI) examples illustrating the operation of an example "Day 1" content-interaction module. Specifically, FIGS. 4A-I illustrate an example new-content-interaction module, and FIG. 41 illustrates an example follow-up-content-interaction module.

FIGS. 5A-G are mobile application UI examples illustrating the operation of an example "Day 2" content-interaction module. Specifically, FIGS. 5A-F illustrate an example new-content-interaction module, and FIG. 5G illustrates an example follow-tin-content-interaction module.

FIGS. 12A-D are mobile application UI examples illustrating the operation of an example content-interaction module far improving eating habits.

DETAILED DESCRIPTION

Figure 1:
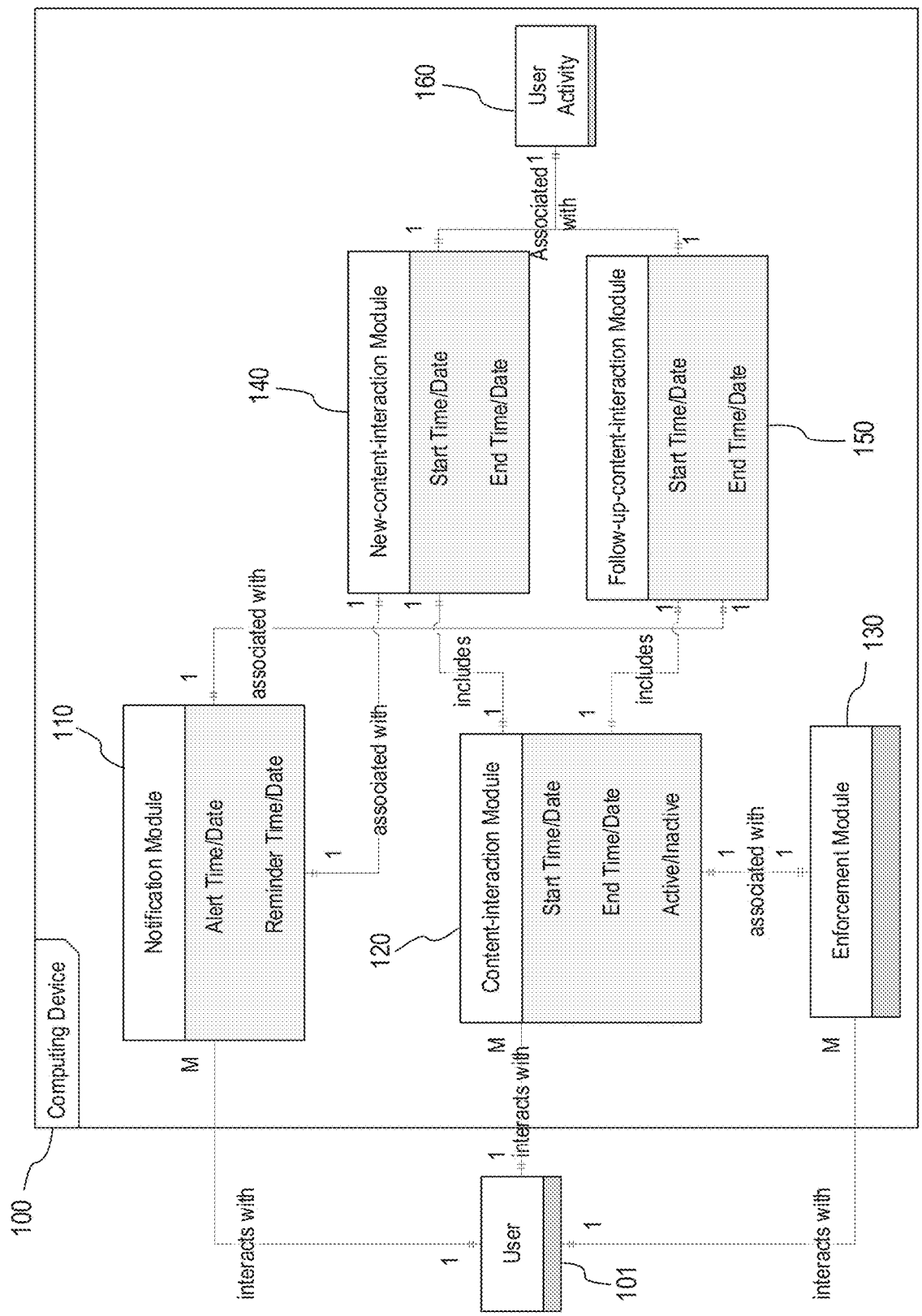
FIG. 1 is a system diagram illustrating example system modules of an example computing device for impriving preparedness fora behavior change effort, such as a quit-smoking attempt, for example.

FIG. 1 is a system diagram illustrating example system modules of an example computing device 100 for improving preparedness far a behavior change effort, such as a quit-smoking attempt, healthy eating, healthy pregnancy behaviors, and the like, for example. The computing device 100 may be configured to improve a user's 101 preparedness for and ultimate success with the behavior change effort. The computing device 100, with the example timing mechanisms and example access rules disclosed herein, may enable an increase in users success.

For example, the computing device 100, as disclosed herein, may enable an about 90% user engagement rate (e.g., adherence) through a 14-day program implementation for smoking cessation. The example timing mechanisms and example access rules disclosed herein, may enable an increase in users' quit-smoking attempts and may enable a significant percentage of users (e.g., over 20% of users) to actually successful quit smoking 30-days after a 14-day device implementation. The computing device 100 may be configured to engage a user 101 for any other suitable time period to improve preparedness for a quit-smoking attempt.

The computing device 100 may be configured by an application (e.g., executable instructions) executing on the computing device 100. The computing device 100 may be a smart phone (e.g., an iOS phone or an Android phone), a tablet (e.g., an iOS tablet or an Android tablet), a laptop computer, a desktop computer, or the like. The application executing on computing device 100 may be a mobile application (e.g., executing on an iOS device or an Android device), a client-server-based application (e.g., operating on the computing device 100 in combination with a server computer), a web-based application (e.g., executing in a browser on a smart phone, a tablet, a laptop computer, or a desktop computer), a desktop application (e.g., executing on a laptop computer or a desktop computer).

The user 101 may desire a behavior change. For example, the user 101 may be a smoker who is in a contemplation stage or a precontemplation stage. The user 101 may not yet be prepared to make a quit-smoking attempt. The computing device 100 may be introduced to the user 101 as a part of a smoking cessation intervention to help the user determine whether the user is prepared to make a quit-smoking attempt.

A user 101 may interact with the computing device 100, e.g., via the computing device's 100 system modules such as a content-interaction module 120, a notification module 110, an enforcement module 130. The user 101 may interact with multiple content-interaction modules 120, multiple notification modules 110, and/or multiple enforcement modules 130. The multiple content-interaction modules 120 may be configured to be specifically associated with a particular user 101 in a multi-user system. A different set of multiple content-interaction modules 120 may be configured to be associated with a different user.

The content interaction module 120 may include one or more user interactions related to behavior change, such as smoking cessation for example. The interactions may include information being presented to the user 101, information being collected from the user 101, and/or a combination thereof. For example, the content interaction module may present a thoughtful topic, an engaging concept, and/or a task for the user 101 to complete. The task may be encompassed in the content interaction itself and/or it may relate to activity to be completed apart from the content interaction itself.

The content-interaction module 120 may include a new-content-interaction module 140 and a follow-up-content-interaction module 150. The new-content-interaction module 140 and the follow-up-content-interaction module 150 may be associated with a user activity 160. The new-content-interaction module 140 may precede the follow-up-content-interaction module 150. A content-interaction module 120 may include a new-content-interaction module 140 and not a follow-up-content-interaction module 150.

For example, a content-interaction module 120 may be configured to include a start time. The start time, for example, may be on a first scheduled date. The content-interaction module 120 may be configured to include an end time. The end time, for example, may be on a second scheduled date.

During operation, the module 120 may interact with a user 101 (e.g., only interact with a user 101) between the start time on the first scheduled date and the end time on the second scheduled date. For example, the module 120 may be in an active state between the start time on the first scheduled date and the end time on the second scheduled date. In a first example, the first scheduled date and the second scheduled date may be the same date. To illustrate an example timing, the content-interaction module 120 may be configured to have a start time of 12 am on Oct. 27, 2020 and an end time of 11:59 pm on Oct. 27, 2020. As such, the user 101 may interact with the module 120 between 12 am and 11:59 pm on Oct. 27, 2020 (e.g., interact only between 12 am and 11:59 pm on Oct. 27, 2020).

In a second example, the first scheduled date and the second scheduled date may be two different dates. Here, to illustrate, the content-interaction module 120 may be configured to have a start time of 9 am on Oct. 27, 2020 and an end time of 9 am on Oct. 28, 2020. As such, the user 101 may interact with the module 120 between 9 am on Oct. 27, 2020 and 9 am on Oct. 27, 2020 (e.g., interact only between 9 am on Oct. 27, 2020 and 9 am on Oct. 27, 2020).

A content-interaction module 120 may be configured to include an active or inactive state indicator. The state indicator may have a system default of inactive. During operation, the module 120 may be in the active state between a start time on a first scheduled date and an end time on a second scheduled date ("active state period"). The module 120 may be in the inactive state outside the active state period.

Multiple content-interaction modules 120 may be configured to interact with a user 101 according to a schedule. The schedule may be configured such that only one module at a time may be in the active state.

Figure 2:
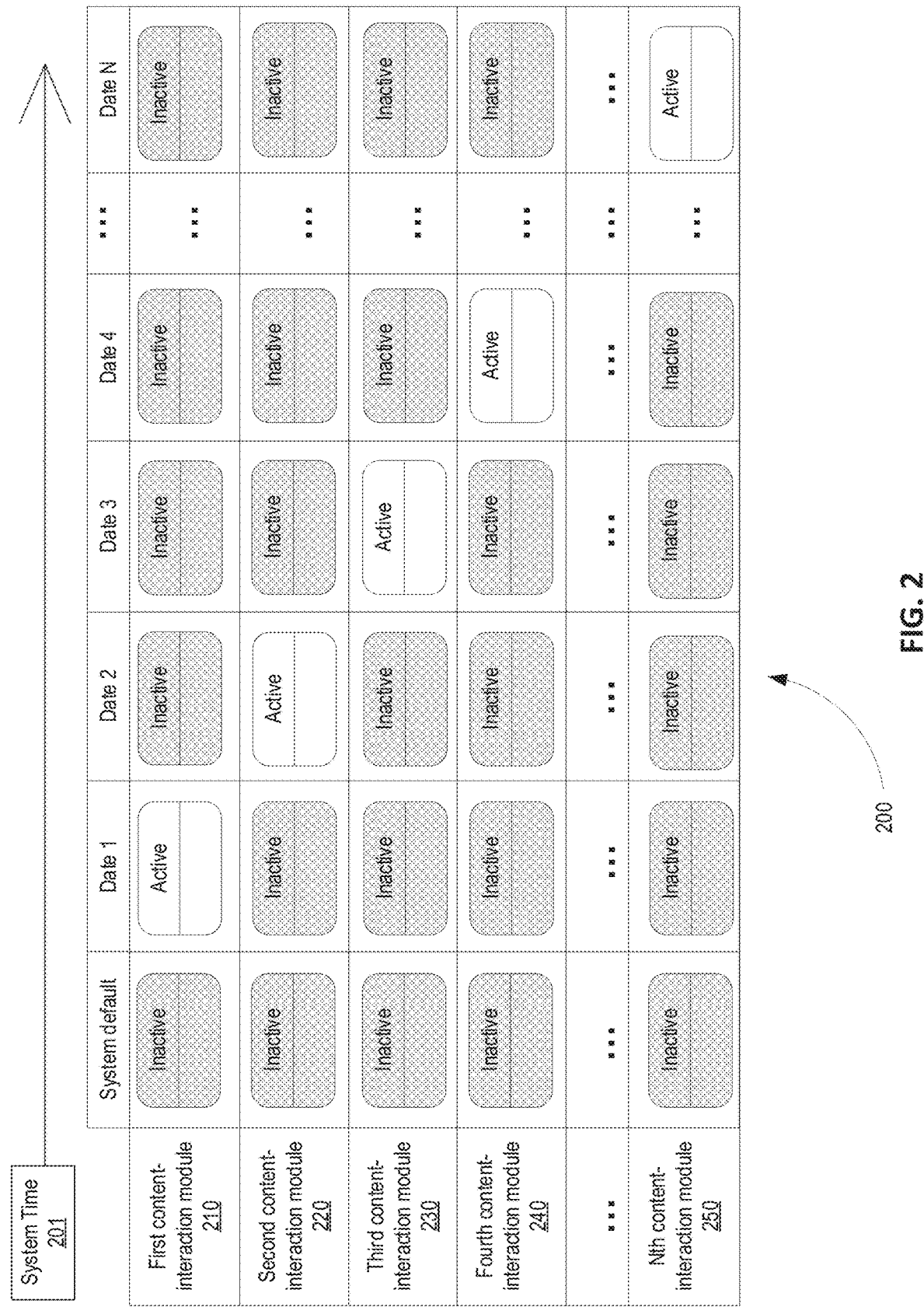
FIG. 2 is a timing diagram for example content-interaction modules.

FIG. 2 is a timing diagram for example content-interaction modules. An example schedule 200 may be associated with multiple content-interaction modules (such as the module 120). There are first content-interaction module 210, second content-interaction module 220, third content-interaction module 230, fourth content-interaction module 240, and modules through Nth content-interaction module 250. The modules are associated with chronologically ordered dates Date 1, Date 2, Date 3, Date 4, and other dates through Date N, respectively.

Each of such modules may be configured to be in the inactive state as a system default. For example, modules 210, 220, 230, 230, 240, and other modules through module 250 are configured to be in the inactive state as a system default.

Each of such modules may be scheduled to transition to the active state at a start time on a scheduled date. For example, modules 210, 220, 230, 240, and modules through module 250 are scheduled to transition from the inactive state to the active state at a start time on Date 1, Date 2, Date 3, Date 4, and other dates through Date N, respectively, under a timeline, e.g., system time 201 of a computing device 100.

Each of such modules may be scheduled to transition to the inactive state at an end time on the same scheduled date. For example, module 210 is scheduled to transition to the inactive state at an end time on Date 1 and remain in the inactive state from Date 2 through Date N. Modules 220, 230, 240, and modules through module 250 are shown to be scheduled for a corresponding transition.

During the period a module is in the active state, the rest of the modules may remain in the inactive state. For example, during the period on Date 1 between the start time and the end time, module 210 is in the active state and modules 220, 230, 240, and modules through modules 250 remain in the inactive state. A corresponding system behavior is shown to be configured for Date 2, Date 3, Date 4, and other dates through Date N.

In the schedule 200, the dates may be on consecutive days. For example, content-interaction modules 120 shown in FIGS. 4A-J and 5A-G may be scheduled for two consecutive days. The dates may be spaced out in a repeating pattern, such as every other day or every Tuesday. The dates may be spaced out in any other pattern. The dates may also be spaced out in no pattern, for example.

The start times of the multiple content-interaction modules 120 scheduled to interact with a user 101 may be a same respective time of day. For example, content-interaction modules 120 shown in FIGS. 4A-J and 5A-G may be scheduled to start at 12 am on each of the two consecutive days.

The end times of such multiple content-interaction modules 120 may be a same respective later time of day on the corresponding days. For example, content-interaction modules 120 shown in FIGS. 4A-J and 5A-G may be scheduled to end at 11:59 pm on each of the two consecutive days.

Referring now to FIG. 1, a new-content-interaction module 140 that may be included in the content-interaction module 120. FIGS. 4A-I and FIGS. 5A-F illustrate such new-content-interaction modules. The new-content-interaction module 140 may be configured to include a corresponding start time on a scheduled date, and a corresponding end time on a second scheduled date. For example, the new-content-interaction module 140 may be configured to include a start time on a first scheduled date of 12 am, Oct. 27, 2020 and an end time on a second scheduled date of 4:59 pm, Oct. 27, 2020. Under such configuration, the first scheduled date and the second scheduled date for the module 140 are configured to be the same date.

A follow-up-content-interaction module 150 that may be included in the content-interaction module 120. FIG. 4J and FIG. 5G illustrate such follow-up-content-interaction modules. The follow-up-content-interaction module 150 may be configured to include a corresponding start time on a first scheduled date, and a corresponding end time on a second scheduled date. The follow-up-content-interaction module 150 may be configured to include a corresponding start time on a first scheduled date of 5 pm, Oct. 27, 2020 and an end time on a second scheduled date of 11:59 pm, Oct. 27, 2020. Under such configuration, the first scheduled date and the second scheduled date for the module 150 are configured to be the same date.

Under such configurations, the module's 140 end time closely precedes the module 150's start time. The module's 140 end time may also be configured to precede the module's 150 start time by a time gap, e.g., 5 pm, Oct. 27, 2020.

Accordingly, under such configurations, the module's 120 start time and date may be configured with the module 140's start time and date, namely, 12 am, Oct. 27, 2020. The module's 120 end time and date may be configured with the module's 150 end time and date, namely, 11:59 pm, Oct. 27, 2020.

A module 140 may also include a corresponding inactive or active state indicator. A module 150 may also include a corresponding inactive or active state indicator.

An enforcement module 130 may be associated with a content-interaction module 120. The module 130 may be configured to enforce content interaction rules for the module 120. A user 101 may access a content module in the active state. The user 101 may be prevented from accessing the content module in the inactive state.

An enforcement module 130 may be configured to enforce content interaction rules specifically for a new-content-interaction module 140 that may be included in a content-interaction module 120 and/or specifically for a follow-up-content-interaction module 150 that may be included in a content-interaction module 120. The content interaction rules may be implemented according to the overall enforcement effect desired.

Figure 9B:
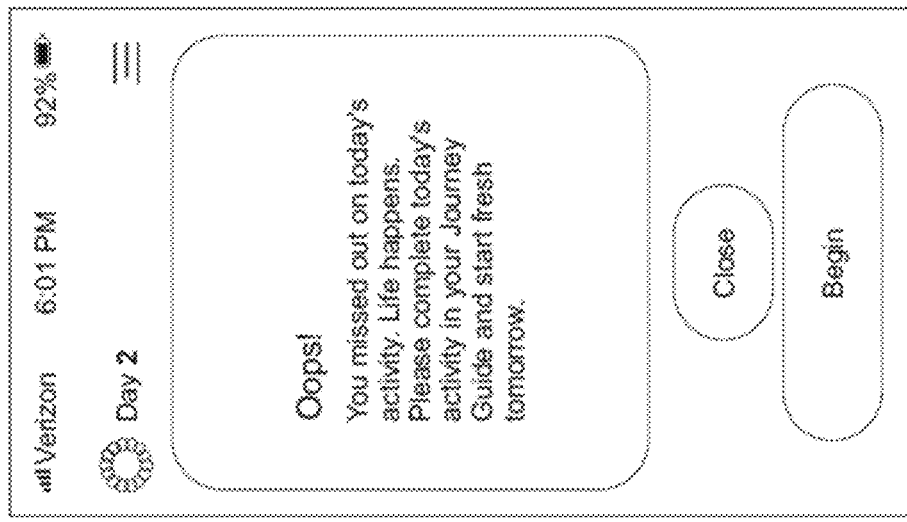
FIGS. 9A-B are mobile application UI examples illustrating the operation of an example enforcement module.
Figure 9A:
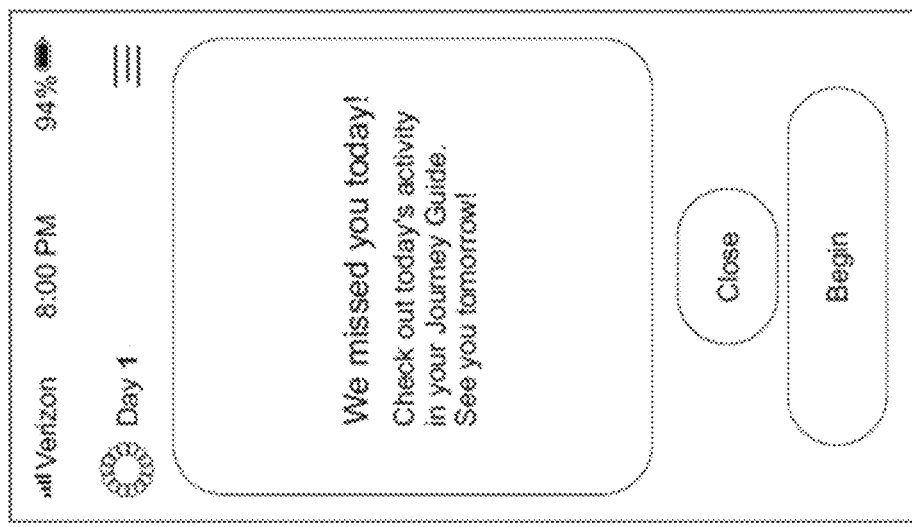

In one example rule, in the case where a user 101 missed accessing the module 140 between the module's 140 start time and end time, e.g., that are scheduled on the same date, the user 101 may be prevented from accessing the module 140 after the module's 140 end time. In this example, the module 130 may detect such attempt by the user 101 and may determine not to navigate the user 101 to the module 140. As shown in FIG. 9A or FIG. 9B, the module 130 may present a message informing the user 101 he/she missed the scheduled user activity and he/she may access the user activity for the next scheduled date. In this example, the module 130 may permit the user 101 to access the module 150.

In another example rule, in the case where a user 101 missed accessing the module 140 between the module's 140 start time and end time, e.g., that are scheduled on the same date, the user 101 may be prevented from accessing the entire content-interaction module 120. That is, the user 101 is prevented not only from accessing the module 140 in such case but also from accessing the module 150 through the next scheduled content-interaction module's 120 start time. For example, even when the user 101 attempts to access the module 150 before the module's 150 end time, the user 101 is still prevented from accessing the module 150.

In another example rule, in the case when a user 101 missed accessing the module 140 between the module's 140 start time and end time, e.g., that are scheduled on the same date, the user 101 is permitted to access the module 140 until the module's 150 end time. Similarly, in the case when a user 101 missed accessing the module 150 between the module's 150 start time and end time, e.g., that are scheduled on the same date, the user 101 is permitted to access the module 150 until the module's 150 end time. In such example, in the case when a user 101 does not access the module 140 before the module's 150 start time, the user 101 may be prevented from accessing the module 150 until the user 101 has accessed the module 140 (e.g., even when the module 150 is in the active state).

A notification module 110 may be associated with a new-content-interaction module 140. The module 110 may be configured to send a notification to the user 101 associated with the content-interaction module 120 that includes the module 140, to alert the user 101 to access the module 140 as (a "trigger"). The notification may be sent at a predefined alert time associated with the module 140, e.g., the start time of the module 140 or a time between the start time and the end time of the module 140. The predefined alert time may be defined by the user 101.

The notification may present a message designed to catch the user's 101 attention and interest and start to engage with the associated new-content interaction module 140. For example, FIGS. 6A-B illustrate the alert notification messages that correspond to the new-content-interaction modules 140 illustrated in FIGS. 4A-I and 5A-F, respectively.

A notification module 110 may be associated with a follow-up-content-interaction module 150. The module 110 may be configured to send a notification to the user 101 associated with the content-interaction module 120 that includes the module 150, to access the module 150 as (a "trigger"). The notification may be sent at a predefined alert time associated with the module, e.g., the start time of the module 150 or a time between the start time and the end time of the module 150.

Figure 7A:
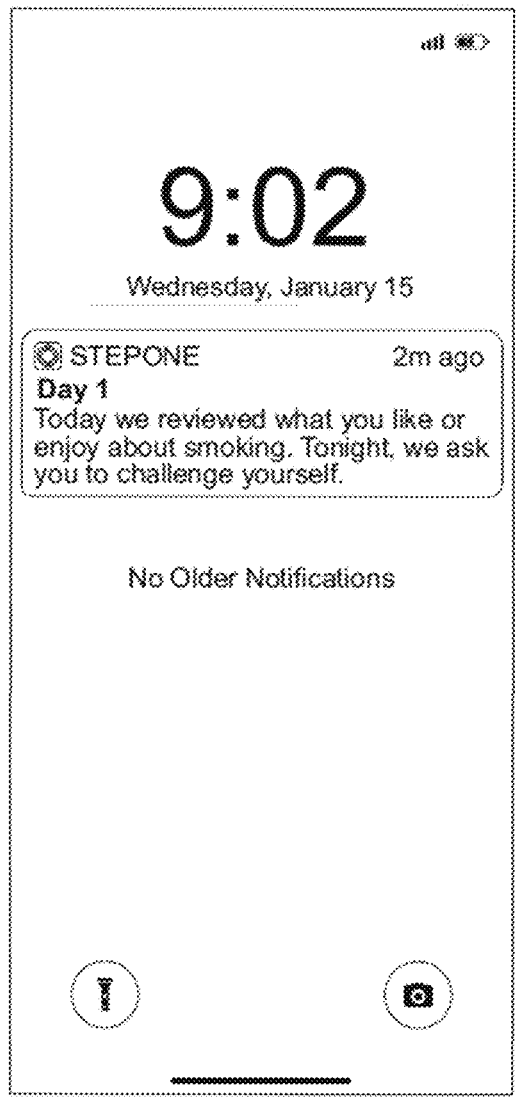
Figure 7B:
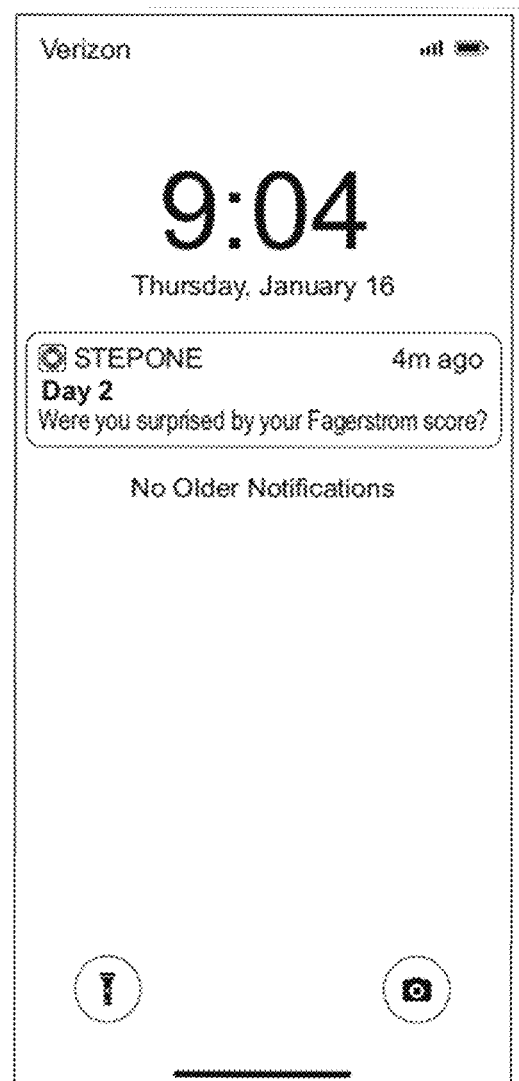

The notification may present a message designed to catch the user's 101 attention and interest and start to engage with the associated follow-up-content interaction module 150. For examples, FIG. 7A-B illustrate the alert notification messages that correspond to the follow-up-content-interaction modules 150 illustrated in FIG. 4J and FIG. 5G, respectively.

A notification module 110 may also be configured to send a notification to the user 101, to remind the user 101 to access the module 150.

Figure 3:
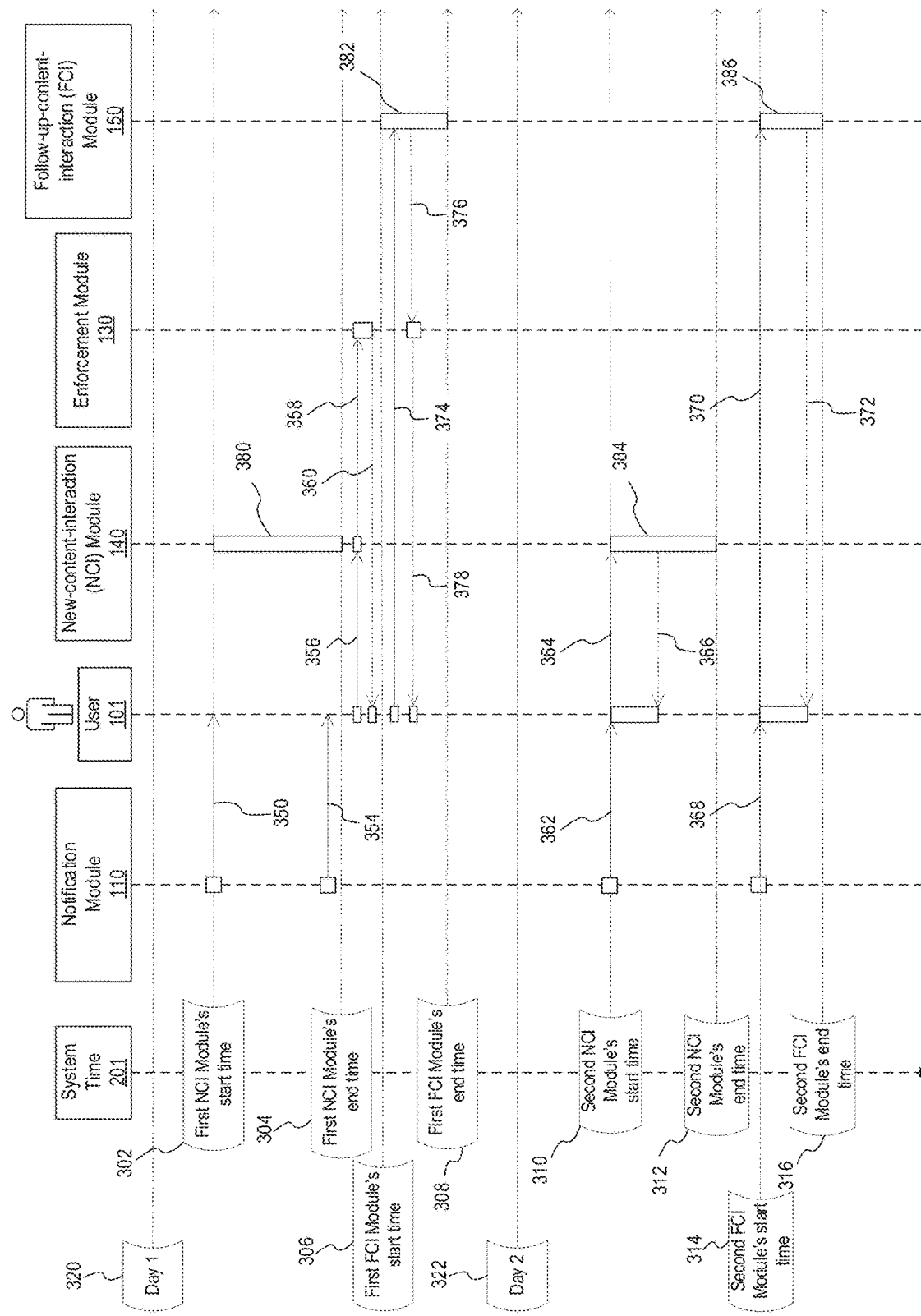
FIG. 3 is a system diagram illustrating an example operation of example system modules of an example computing device for improving preparedness for 3, quit-smoking attempt.

FIG. 3 is a system diagram illustrating a timing aspect of the operation of the key system modules of an example computing device for improving preparedness for a quit smoking attempt. On a timeline represented by a system rime 201 (e.g., associated with a computing device 100), 320 on the system time 201 indicates the beginning of the Day 1 (e.g., 12 am on Day 1). 302 on the system rime 201 indicates a first new-content-interaction (NCI) module's 140 start time. 304 on the system time 201 indicates the first NCI module's 140 end time. 306 on the system time 201 indicates the first follow-up content-interact ion (FCI) module's 150 start time. 308 on the system time 201 indicates the first follow-up-content-interaction (FCI) module's 150 end time.

At 302, the first NCI module 140 transitions from the inactive state (e.g., a system default) into the active state 380. Also at 302, at step 350, a notification module 110 associated with the first NCI module 140 sends an alert notification to a user 101. In this example, the user 101 does not respond to the notification at 302.

At a time before 304 on the system time 201, at step 351, the notification module 110 associated with the first NCI module 140 sends a reminder notification to the user 101. The user 101 again does not respond to the notification.

At 304, the first NCI module transitions from the active state into the inactive state.

At a time after 304 and before 306, the user 101, at step 356, attempts to access the first NCI module 140, which is in the inactive state. Being in tire inactive stare, at step 358, the first NCI module 140 redirects the user's 101 access attempt to an enforcement module 130 associated with a first content interaction module 120 (not shown) including the first NCI module 140. The enforcement module 130, m such example, is configured to enforce content interaction rules for the first content-interaction module 120 solely based on the first NCI module 140, as described in FIG. 1. At step 360, after having detected the attempted access, the enforcement module 130 presents a message (e.g., the message shown in FIGS. 9A-B).

At 306, the first FCI module 150 transitions from the inactive state (e.g., a system default) into the active state 382.

At a time after 306 and before 308, at step 374, the user 101 attempts to access the first FCI module 150, which is in the active state. As described herein, die enforcement module is configured to enforce content interaction rules for the first content-interaction module 120 solely based on the first NCI module 140. Given the fast NCI module 140 is in rite inactive state, the user 101 is prevented from accessing the first FCI module 150 even though the first FCI module 150 is m the active state. Accordingly, at step 376, the first FCI module 150 redirects the user's 101 access attempt to the enforcement module 130. After detecting the attempted access, at step 378, the enforcement module 130 presents a message (e g, the message shown in FIGS. 9A-B).

At 308, the first FCI module 150 transitions from the active state to the inactive state without having been accessed from the user 101.

322 on the system time 201 indicates the beginning of the Day 2 (e.g., 12 am on Day 2). 310 on the system time 201 indicates a second new-content-interaction (NCI) module's 140 start time. 312 on the system time 201 indicates the second NCI module's 140 end rime. 314 on the system time 201 indicates the second follow-up-content-interaction (FCI) module's 150 start time. 316 on the system time 201 indicates the second follow-op-content-interaction (FCI) module's 150 end tune.

At 310, the second NCI module 140 transitions from the inactive state (e.g., a system default) into the active state 384. Also at 310, at step 362, a notification module 110 associated with the second NCI module 140 sends an alert notification to a user 101. At step 364, the user 101 responds to the notification by accessing the second NCI module 140. In response, at step 366, the second NCI module presents content related to a user activity associated with the second NCI module 140 and the second FCI module 150.

At 312, the second NCI module transitions from the active state into the inactive state.

At 314, the second FCI module 150 transitions from the inactive state (e.g., a system default) into the active state 386. Also at 310, at step 368, a notification module 110 associated with the second FCI module 140 sends an alert notification to the user 101. At step 370, the user 101 responds to the notification by accessing the second NCI module 140. In response, at step 372, the second NCI module 140 presents content related to the user activity associated with the second NCI module 140 and the second FCI module 150.

At 316, the second FCI module 150 transitions from the active suite into the inactive state.

Figures 4A, 4B, 4C, 4D:
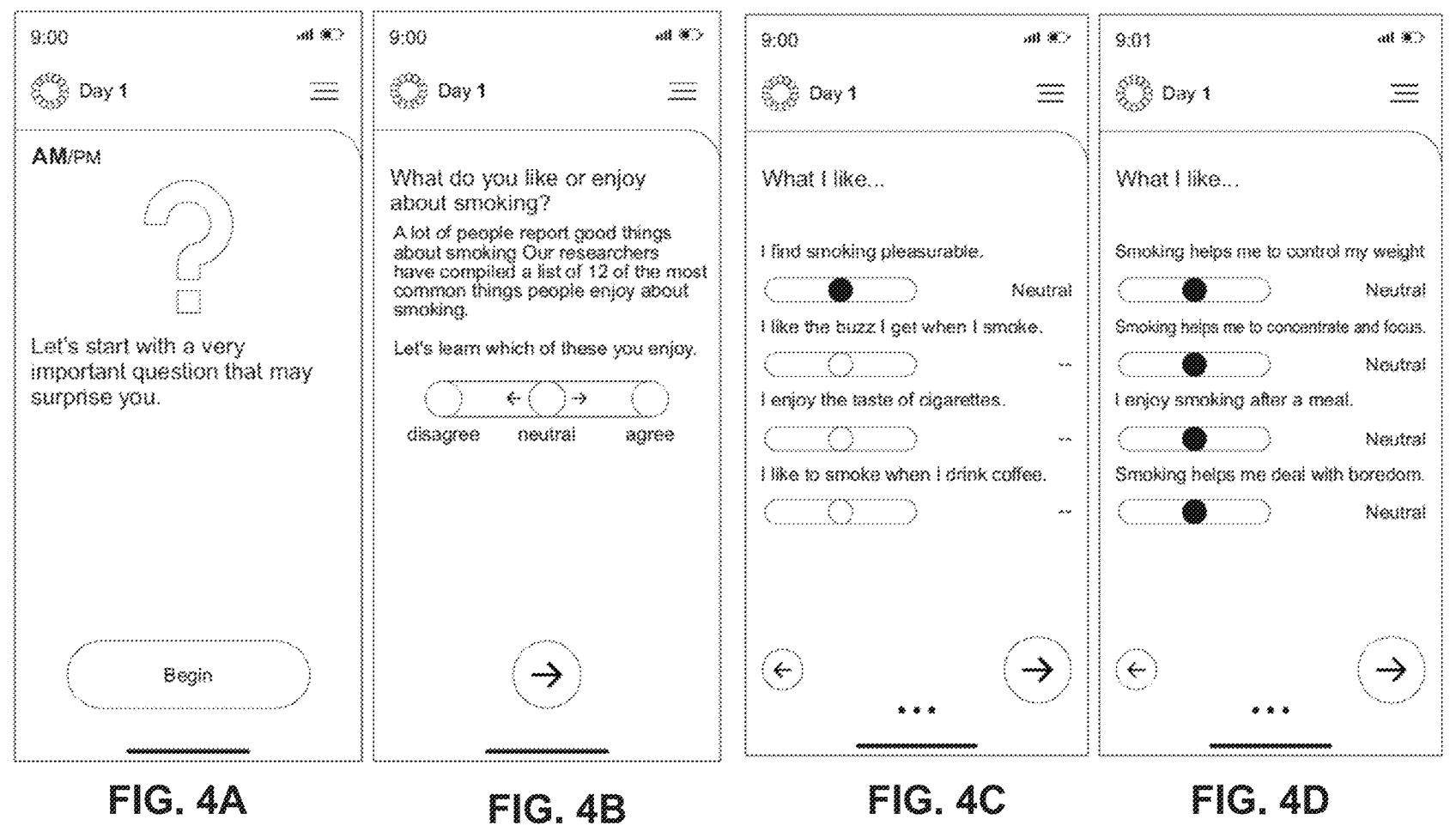
Figures 4E, 4F, 4G, 4H, 4I:
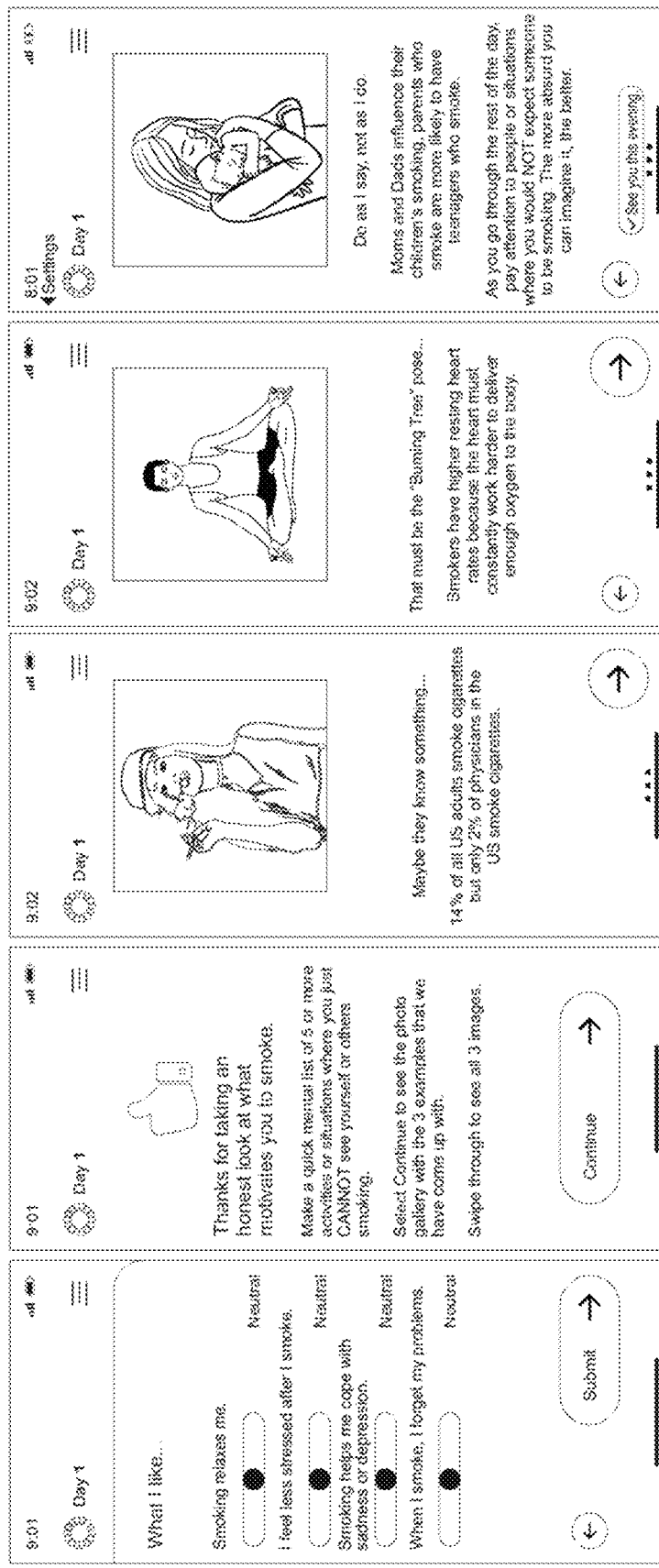
Figure 4J:
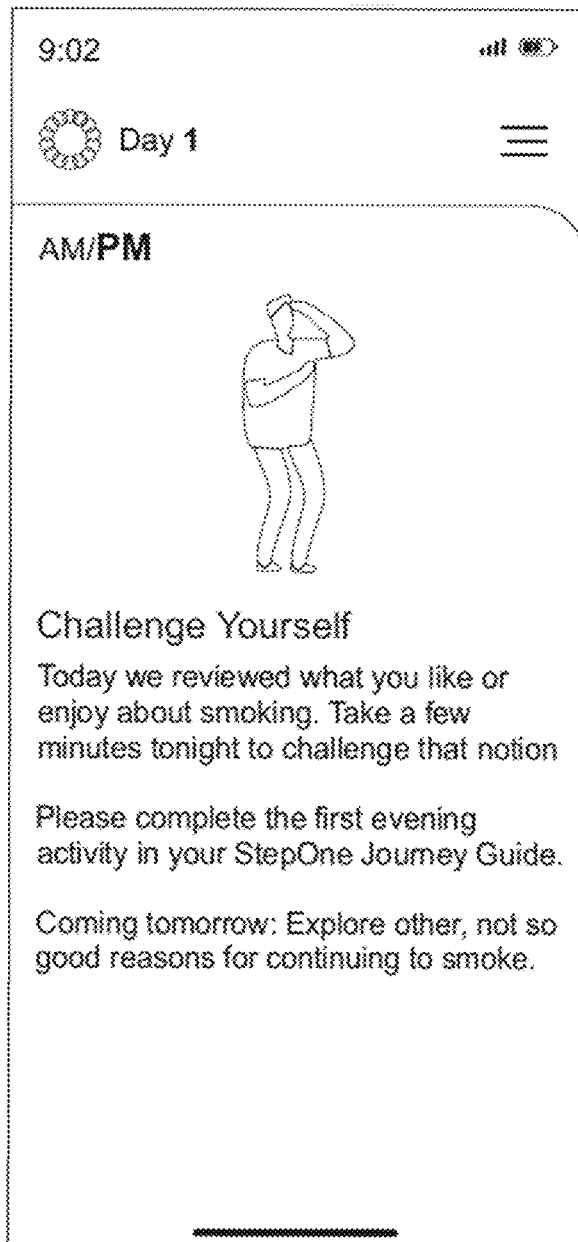
Figure 5G:
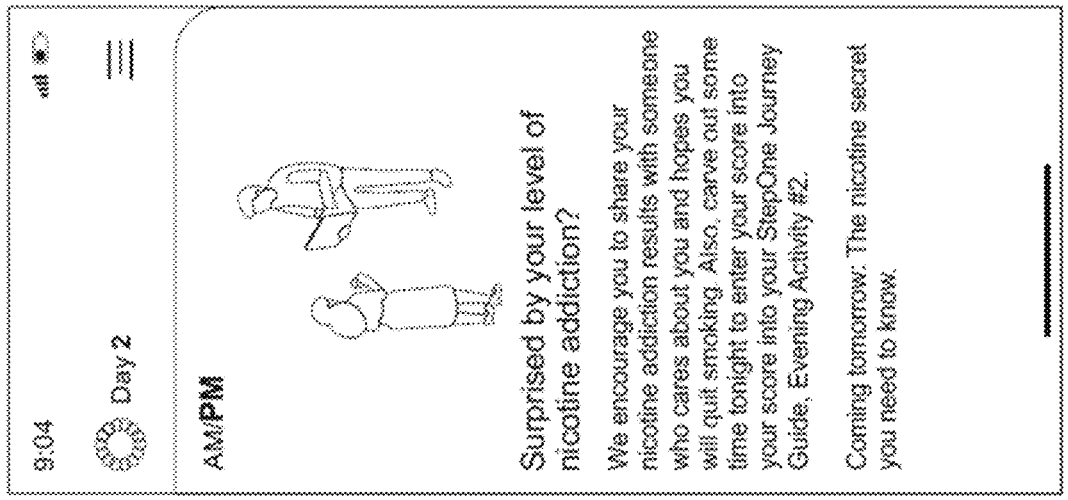

FIGS. 4A-J show a mobile application user interface (UI) examples of the operation of an example content-interaction module 120 of an example computing device 100 for improving preparedness for a quit smoking attempt. The module 120 interacts with a user 101 regarding the user's 101 motivation and reasons for smoking. FIGS. 4A-1 illustrate an example new-content-interaction module 140 included in the module 120. And FIG. 4J illustrates an example follow-up-content-interaction module 150 included in the module 120. The module 140 as shown in FIGS. 4A-4F poses a series of survey questions to the user 101 about what the user 101 likes or enjoys about smoking. In such manner, the module 140 engages the user 101 in performing an "action", namely, a user activity 160 of answering questions related to the user's 101 motivation and reasons for smoking. The module 140 also presents images of surprising smokers in FIGS. 4G-I. These images may serve as a psychological "reward" (e.g., due to its unexpected nature) for the action the user 101 performed in the user activity 160. The reward engenders the user's 101 attachment to the computing device 100 due to an implicit promise of future rewards. In such manner, the user's 101 engagement with the computing device 100 is improved.

The example new-content-interaction module 140 as shown in FIGS. 4A-I may be configured to execute in the morning of a day while the example follow-up-content-interaction module 150 as shown in FIG. 4J may be configured to execute in the evening of the same day. FIG. 4J illustrates a review with die user 101 of the user activity 160 performed by die user 101 earlier in the day. The module 140 as shown in FIGS. 4A-I and the module 150 as shown in FIG. 4J may also be configured to execute without a time gap between them both in the morning of the same day or both in the evening of the same day. The module 140 and the module 150 may also lie configured to execute back-to-back with no time gap between them at any predefined time of a day. The module 140 and the module 150 may also be configured to execute on two different days, such as two consecutive days or with a period of one or more days between the two different days.

FIGS. 5A-G illustrate mobile application user interface (UI) examples of the operation of an example content-interaction module 120 of an example computing device 100 for improving preparedness for a quit smoking attempt. The module 120 interacts with a user 101 regarding the user's 101 dependence on nicotine.

Figure 5F:
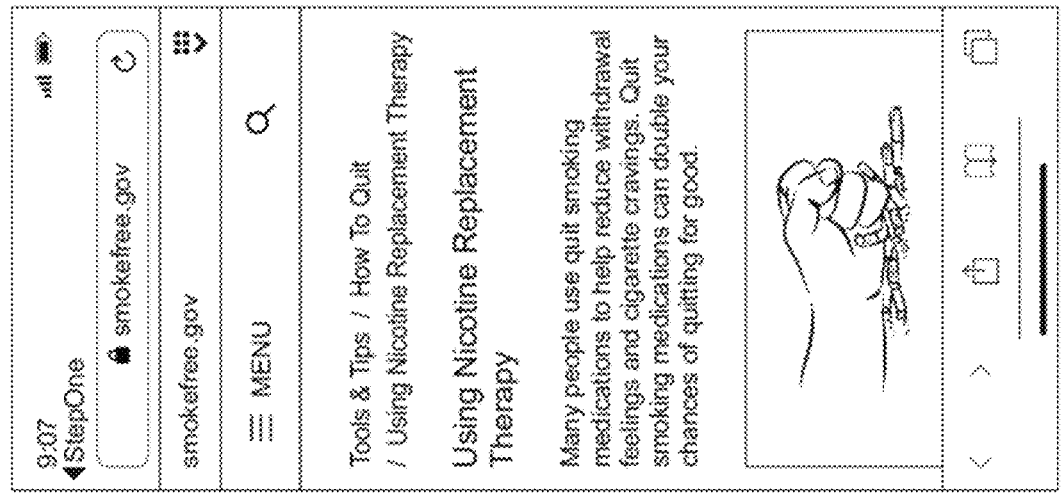
Figure 5E:
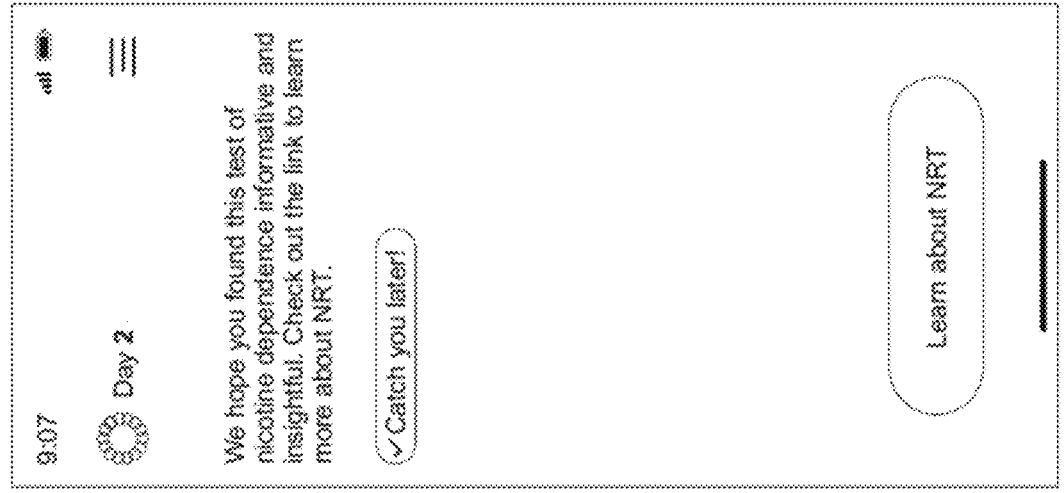
Figure 6A:
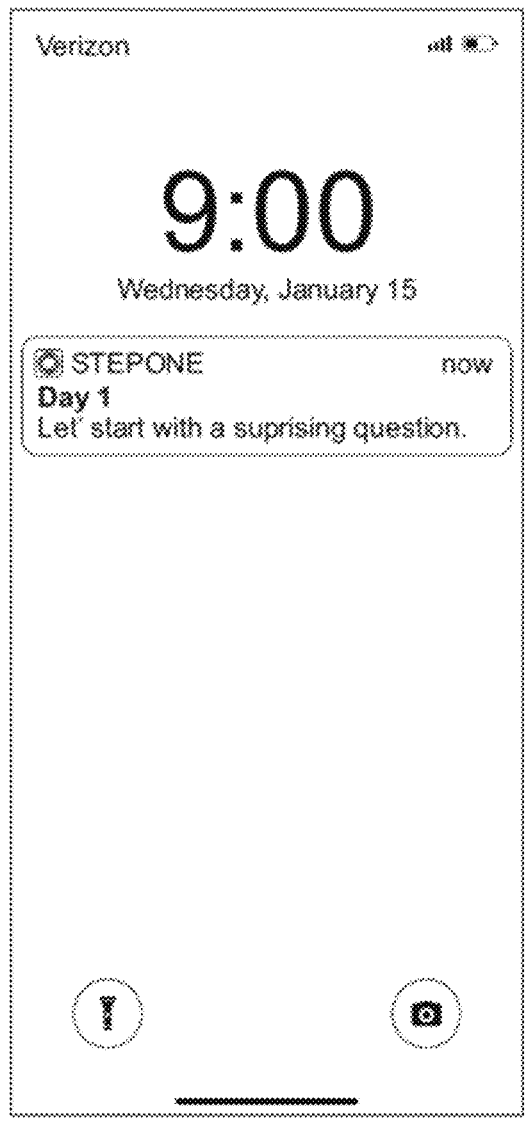
FIGS. 6A-8B are mobile application UI examples illustrating the operation of an example notification module.
Figure 6B:
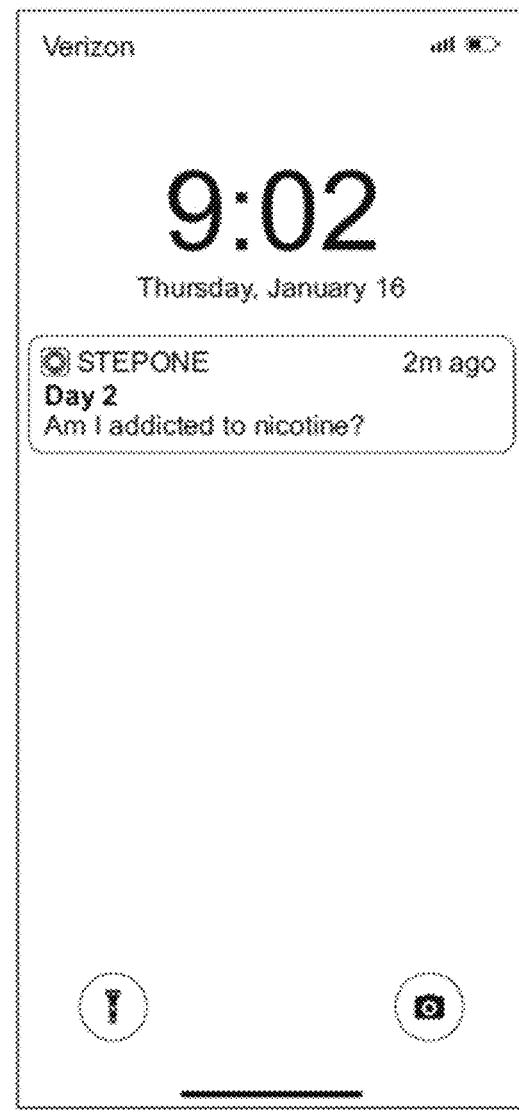

FIGS. 5A-F illustrate an example new-content-interaction module 140 included in the module 120. FIG. 5G illustrates an example follow-up-content-interaction module 150 included in the module 120. The module 140 as illustrated in FIGS. 5A-B presents the Fagerstrom Test. FIGS. 5C-D illustrate the user's Fagerstrom Test score and associated recommendations being presented to the user 101 based on the user's 101 answers. In such manner, the module 140 engages the user 101 in performing an action, namely, a user activity 160 of answering questions related to the user's 101 dependence on nicotine. FIGS. 5D-F illustrate the module 140 presenting additional resources related to the nicotine replacement treatment (NRT) recommendation. These resources may serve as a psychological reward for the action the user 101 just performed. FIG. 5G illustrates an example follow-up-content-interaction module 150 where a review with the user 101 of the user activity 160 performed by the user 101 is presented.

FIGS. 6A-8B are mobile application UI examples illustrating the operation of an example notification module of an example computing device for in preparedness for a quit-smoking attempt. For example, a notification module 110 may be associated with a new-content-interaction module 140. The notification may present a message designed to catch the user's 101 attention and interest and start to engage with the associated new-content interaction module 140. For examples, FIG. 6A-B illustrate the alert notification messages that correspond to the new-content-interaction modules 140 illustrated in FIGS. 4A-4I and 5A-5F, respectively.

For example, a notification module 110 may be associated with a follow-up-content-interaction module 150. Here, the notification may present a message designed to catch the user's 101 attention and interest and start to engage with the associated follow-up-content interaction module 150. For example, FIG. 7A-B illustrate the alert notification messages that correspond to the follow-up-content-interaction modules 150 illustrated in FIG. 4J and FIG. 5G, respectively.

Figure 8B:
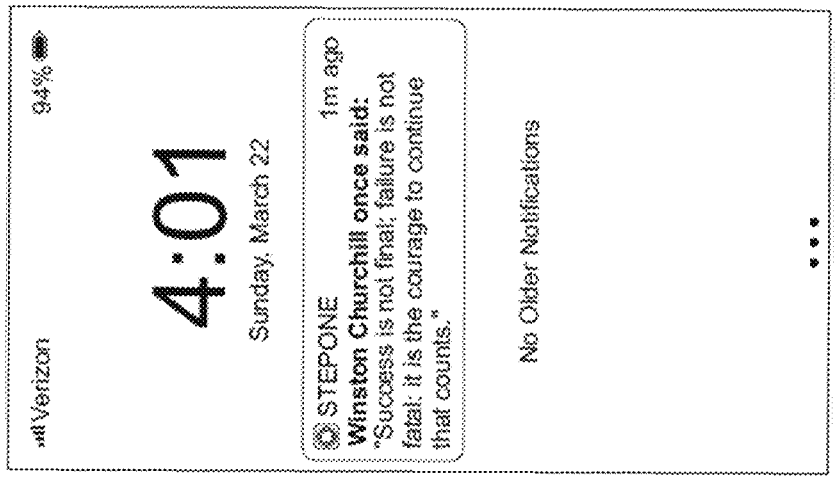
Figure 8A:
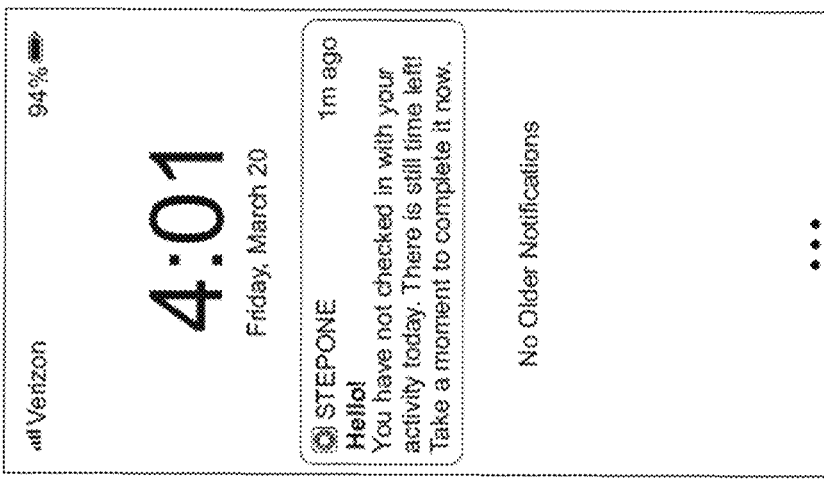

FIGS. 8A-B illustrate an example notification module 110 that may be associated with a new-content interaction module 140 and/or a follow-up content interaction module 150.

FIGS. 9A-B are mobile application UI examples illustrating the operation of an example enforcement module of an example computing device for improving preparedness for a quit-smoking attempt. An enforcement module 130 may be configured to enforce content interaction rules specifically for a new-content-interaction module 140 and/or a follow-up-content-interaction module 150. The enforcement module 130 may explain the specific timing and access rules to the user 101. The enforcement module 130 may relate a sense of losing out on content to the user 101 and consequently drive improved user adherence to proper operation of the computing device 100 and the corresponding mobile application. For example, the enforcement module 130 may include a user message indicating that the user's non-compliance with the access rules results in the user losing out on experiencing an activity of the content-interaction module 120.

Figure 10A:
FIGS. 10A-C are mobile application UI examples illustrating the operation of an example content-interaction module for improving behaviors for a healthy pregnancy.
Figure 10B:
Figure 10C:

FIGS. 10A-C are mobile application user interface (UI) examples illustrating the operation of an example content-interaction module 120 for improving behaviors for a healthy pregnancy. The module 120 may interact with a user 101 regarding the user's 101 sleep-related behaviors. FIGS. 10A-B illustrate an example new-content-interaction module 140 included in the module 120. FIG. 10C illustrates an example follow-up-content-interaction module 150 included in the module 120. The module 140 as shown in FIGS. 10A-B poses a question to a user 101 about a sleep goal and suggests a number of activities the user 101 can try to achieve the goal. In an example, as shown in FIG. 10C, if the user 101 selects to try deep breathing, the module 150 follows up and inquires about the deep breathing's effect on the user 101. In such manner, the modules 140 and 150 engages the user 101 in performing an "action", namely, a user activity 160 of trying deep breathing while the user 101 is engaging with the computing device. Such action and the associated effect on the user 101 may motivate the user 101 to perform a user activity 160 of trying deep breathing apart from the modules 140 and 150 (e.g., when the user 101 is not engaging with the computing device 101). The module 150 also provides resources about stress relieving products and shows an image of a person sound in sleep. Such resources may serve as a psychological reward for the action the user 101 just performed.

Figure 11C:
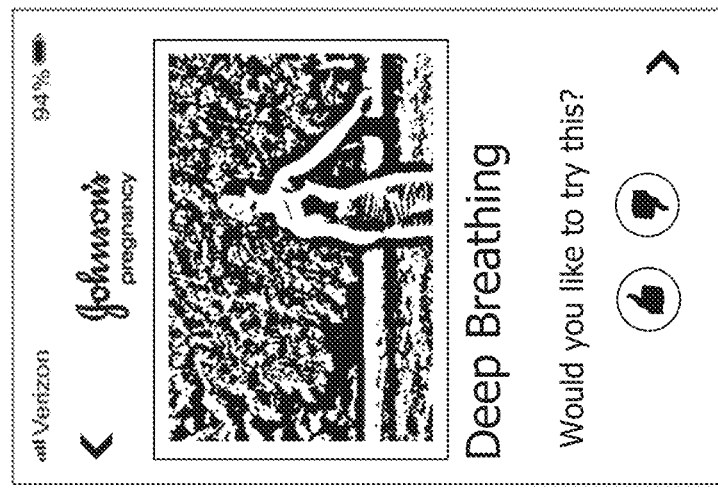
FIGS. 11A-C are mobile application UI examples illustrating the operation of an example notification module for improving behaviors for a healthy pregnancy.
Figure 11B:
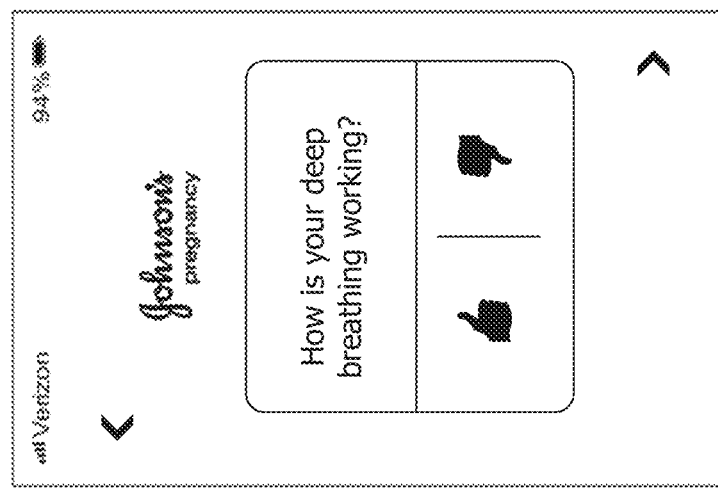
Figure 11A:
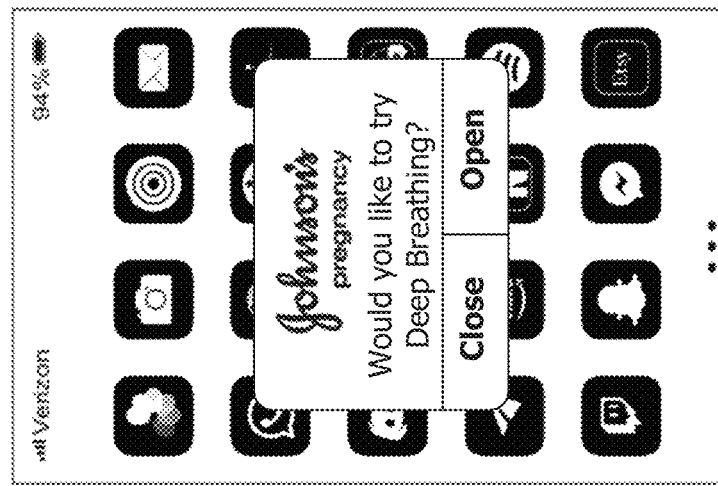

FIGS. 11A-C are mobile application UI examples illustrating the operation of an example notification module improving behaviors for a healthy pregnancy. For example, a notification module 110 may be associated with the new-content-interaction module 140 and the follow-up-content-interaction module 150. The notification may present a message designed to catch the user's 101 attention and interest and start to engage with the associated the modules 140 and 150. For examples, FIG. 11A illustrates an alert notification message (e.g., outside of the mobile application UI) that corresponds to the modules 140 and 150 illustrated in FIGS. 10A-C. FIG. 11B illustrates an alert notification message (e.g., within the mobile application UI) that corresponds to the modules 140 and 150 illustrated in FIGS. 10A-C. FIG. 11C illustrates an alert notification message for a next content module 120 (e.g., scheduled to activate on the day after the content module 120 shown in FIGS. 10A-C).

FIGS. 12A-D are mobile application UI examples illustrating the operation of an example content-interaction module for improving eating habit. The module 120 may interact with a user 101 regarding the user's 101 eating habits. FIGS.

12A-C illustrate an example new-content-interaction module 140 included in the module 120. FIG. 12D illustrates an example follow-up-content-interaction module 150 included in the module 120. The module 140 as shown in FIGS. 12A-B poses questions to a user 101. In such manner, the module 140 engages the user 101 in performing an action, namely, a user activity 160 of understanding his/her eating habits. The module 140 also engages the user 101 in a user activity 160 of sharing his/her commitment with others. The module 150 as shown in FIG. 12D prompts a user 101 regarding his/her performance.

Figure 13:
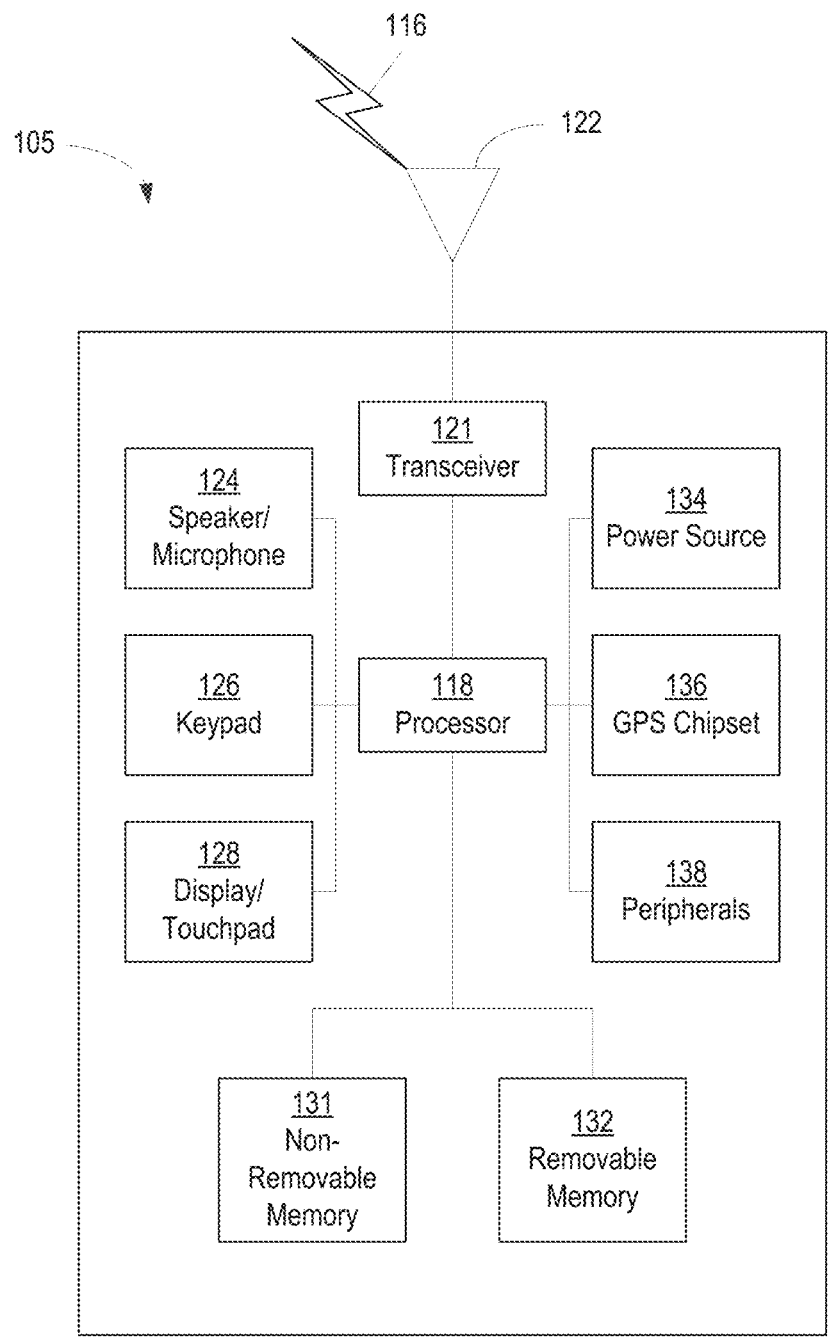
FIG. 13 is a system diagram illustrating an example computing device.

FIG. 13 is a system diagram illustrating an example computing device 105 for improving preparedness for a quit smoking attempt. As shown in FIG. 13, the computing device 105 may include a processor 118, a transceiver 121, a transmit/receive element 121, a speaker/microphone 124, a keypad 126, a display/touchpad 128, non-removable memory 131, removable memory 132, a power source 134, a global positioning system (GPS) chipset 136, and/or other peripherals 138, among others. It will be appreciated that the computing device 105 may include any sub-combination of the foregoing elements while remaining consistent with an embodiment.

The processor 118 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 118 may perform signal coding, data processing, power control, input/output processing, and/or any other functionality that enables the computing device 105 to operate in a wireless environment. The processor 118 may be coupled to the transceiver 121, which may be coupled to the transmit/receive element 121. While FIG. 13 depicts the processor 118 and the transceiver 121 as separate components, it will be appreciated that the processor 118 and the transceiver 121 may be integrated together in an electronic package or chip.

The transmit/receive element 121 may be configured to transmit signals to, or receive signals from, a base station over the air interface 116. For example, in one embodiment, the transmit/receive element 121 may be an antenna configured to transmit and/or receive RF signals. In an embodiment, the transmit/receive element 121 may be an emitter/detector configured to transmit and/or receive IR, UV, or visible light signals, for example. In yet another embodiment, the transmit/receive element 121 may be configured to transmit and/or receive both RF and light signals. It will be appreciated that the transmit/receive element 121 may be configured to transmit and/or receive any combination of wireless signals.

The processor 118 of the computing device 105 may be coupled to, and may receive user input data from, the speaker/microphone 124, the keypad 126, and/or the display/touchpad 128 (e.g., a liquid crystal display (LCD) display unit or organic light-emitting diode (OLED) display unit). The processor 118 may also output user data to the speaker/microphone 124, the keypad 126, and/or the display/touchpad 128. In addition, the processor 118 may access information from, and store data in, any type of suitable memory, such as the non-removable memory 131 and/or the removable memory 132. The non-removable memory 131 may include random-access memory (RAM), read-only memory (ROM), a hard disk, or any other type of memory storage device. The removable memory 132 may include a subscriber identity module (SIM) card, a memory stick, a secure digital (SD) memory card, and the like. In other embodiments, the processor 118 may access information from, and store data in, memory that is not physically located on the computing device 105, such as on a server or a home computer (not shown).

The processor 118 may receive power from the power source 134 and may be configured to distribute and/or control the power to the other components in the computing device 105. The power source 134 may be any suitable device for powering the computing device 105. For example, the power source 134 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 118 may also be coupled to the GPS chipset 136, which may be configured to provide location information (e.g., longitude and latitude) regarding the current location of the computing device 105. In addition to, or in lieu of, the information from the GPS chipset 136, the computing device 105 may receive location information over the air interface 116 from a base station and/or determine its location based on the timing of the signals being received from two or more nearby base stations. It will be appreciated that the computing device 105 may acquire location information by way of any suitable location-determination method while remaining consistent with an embodiment.

The processor 118 may further be coupled to other peripherals 138, which may include one or more software and/or hardware modules that provide additional features, functionality and/or wired or wireless connectivity. For example, the peripherals 138 may include an accelerometer, an e-compass, a satellite transceiver, a digital camera (for photographs and/or video), a universal serial bus (USB) port, a vibration device, a television transceiver, a hands free headset, a Bluetooth® module, a frequency modulated (FM) radio unit, a digital music player, a media player, a video game player module, an Internet browser, a Virtual Reality and/or Augmented Reality (VR/AR) device, an activity tracker, and the like. The peripherals 138 may include one or more sensors, the sensors may be one or more of a gyroscope, an accelerometer, a hall effect sensor, a magnetometer, an orientation sensor, a proximity sensor, a temperature sensor, a time sensor; a geolocation sensor; an altimeter, a light sensor, a touch sensor, a magnetometer, a barometer, a gesture sensor, a biometric sensor, and/or a humidity sensor.

Figure 14:
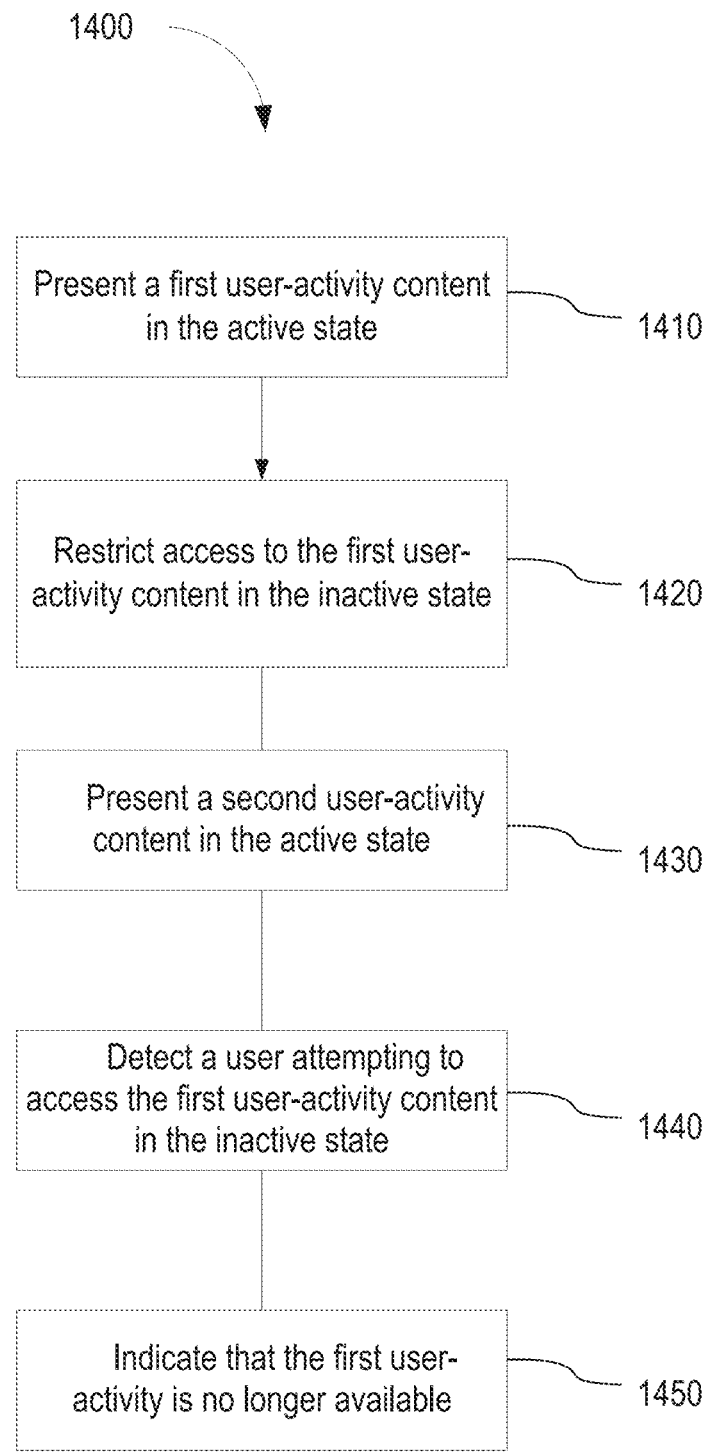
FIG. 14 is a flow diagram illustrating an example computer-implemented method.

FIG. 14 is a flow diagram illustrating an example computer-implemented method 1400 for improving preparedness for a quit-smoking attempt via a plurality of chronologically scheduled content interactions. At 1410, the method 1400 may present a first user-activity content between a first start time on a first scheduled date and a first end time on the first scheduled date (i.e., when the first user-activity content's in the active state). The method 1400 may present the first user-activity content between a third start time on the first scheduled date and a third end time on the first scheduled date, and between a fourth start time on the first scheduled date and a fourth end time on the first scheduled date. In such case, the third start time on the first scheduled date is the same as the first start time on the first scheduled date, the fourth end time on the first scheduled date is the same as the first end time on the first scheduled date.

At 1420, the method 1400 may restrict access to the first user-activity content at the first end time on the first scheduled date (i.e., after the first user-activity content transitions to the inactive state). At 1430, the method 1400 may present a second user-activity content between a second start time on a second scheduled date and a second end time on the second scheduled date, which is after the first scheduled date.

At 1440, the method 1400 may detect a user attempting to access the first user-activity content between the first end time on the first scheduled date and the second start time on the second scheduled date. At 1450, in response to the detection, the method 1400 may indicate to the user that the first user-activity is no longer available on the condition that the first user-activity was not accessed between the first start time on the first scheduled date and the first end time on the first scheduled date.

At 1440, the method 1400 may further detect the user attempting to access the first user-activity content between the third end time of the first schedule date and the fourth end time on the first scheduled date. At 1450, in response to the detection, the method 1400 may indicate that the first content-interaction module is no longer available and that the second content-interaction module will become available on the second scheduled date.

The method 1400 may send an alert notification message to the user alerting the user to access the first content-interaction module at a predefined time before the first end time of the first content-interaction module. In such case, the predefined time may be one of: the first start time of the first content-interaction module, or a time after the first start time of the first content-interaction module.

The method 1400 may send a reminder notification message to the user reminding the user to access the first content-interaction module at a predefined time before the first end time of the first content-interaction module on a condition that the user missed accessing the first content-interaction module between the first start time of the first content-interaction module and the predefined time.

Figure 15A:
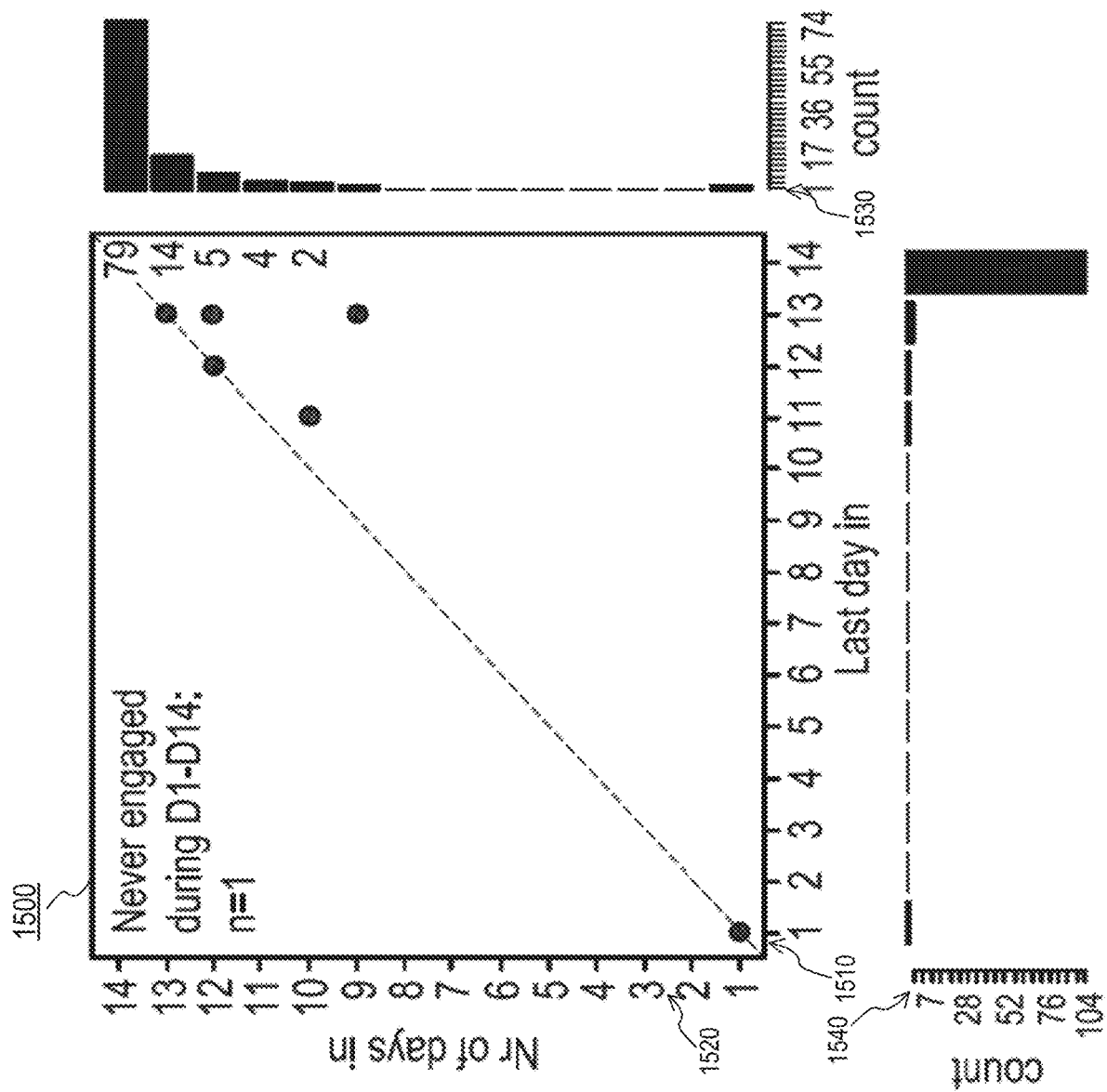
FIGS. 15A-B illustrate an example result (e.g., engagement rate and complete rate, respectively) of user interactions with a 14-day program implementation for smoking cessation
Figure 15B:
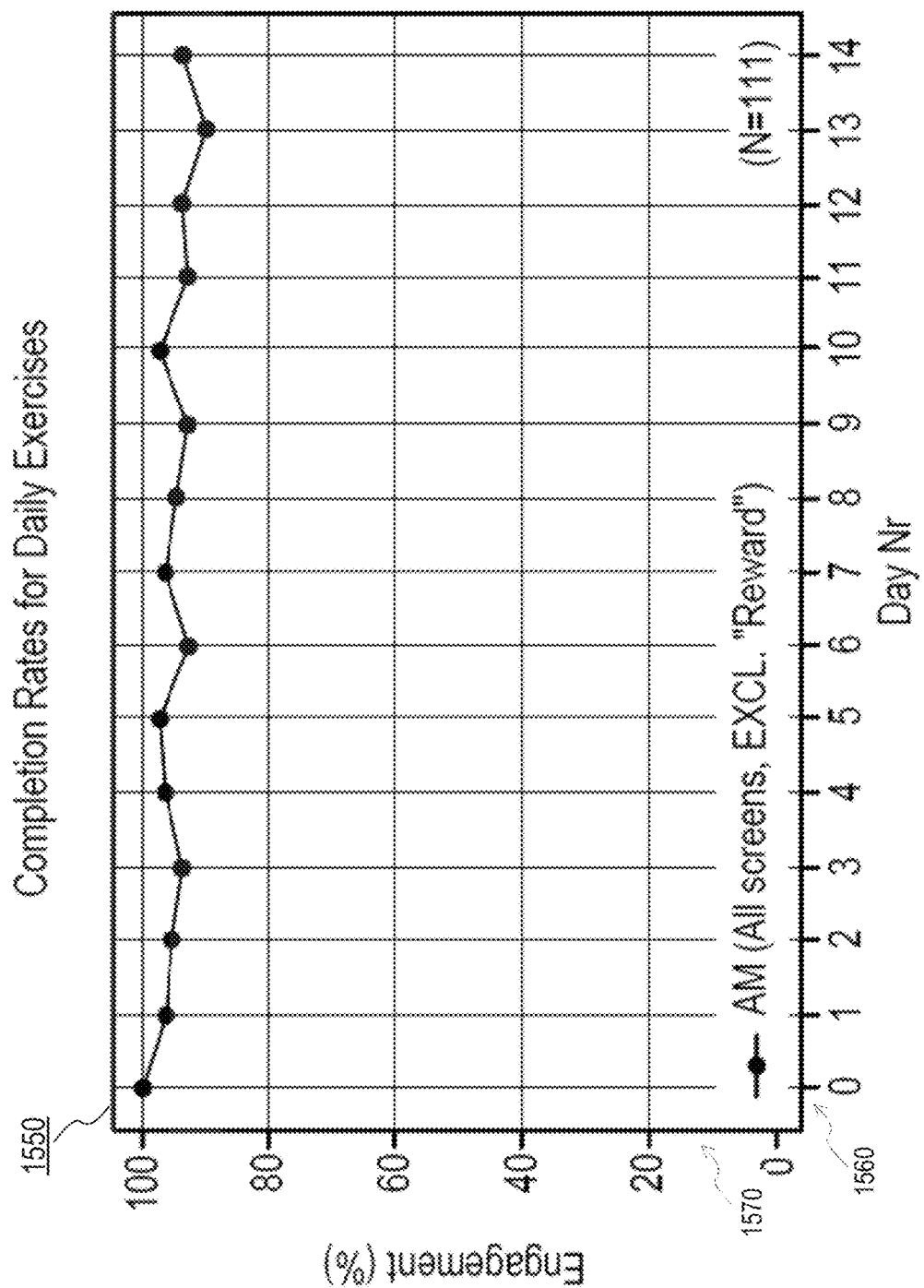

FIGS. 15A-B illustrate an example result (e.g., engagement rate and completion rate, respectively) of user interactions with a 14-day program implementation for smoking cessation (e.g., using the computing device 100). In this example, one hundred and eleven (111) users 101 participated in the 14-day program. The program had high engagement/completion rates, resulted in users' stronger motivation, higher confidence, more readiness for a quit attempt, and resulted in dramatically more transitions from precontemplation or contemplation stages to preparation or action stages.

FIG. 15A illustrates engagement rates of the users in the 14-day program. The engagement rates illustrated relate to the users' interactions in the mornings (AM) of the 14-day period. The users engage in the 14-day program via, inter alia, new-content-interaction modules 140 that activate in the mornings. The chart 1500 includes an axis 1510 and an axis 1520. The axis 1510 represents the last day a user 101 participates in the program. For example, if a user 101 last participates on day 1 of the program, it is represented as a value of 1 on the axis 1510. If a user 101 last participates on day 14 of the program, it is represented as a value of 14 on the axis 1510. The axis 1520 presents the number of days a user 101 engaged with the program. For example, if a user 101 engages with the program on one day in the 14-day period, it is represented as a value of 1 on the axis 1520. If a user 101 engages with the program on 14 days in the 14-day period, it is represented as a value of 14 on the axis 1520.

The chart 1500 is further illustrated via a count 1530 and a count 1540. The count 1530 represents a total count of users that participates in the program for a number of days, which may be between one day and 14 days. For example, as illustrated, there are 79 users, 14 users, 5 users, 4 users, and 2 users that participated in the program for 14 days, 13 days, 12 days, 11 days, and 10 days, respectively. The count 1540 represents a total count of users that last participates in the 14-day program on each day of the 14-day period. For example, as illustrated, there are 104 users (the sum of 79, 14, 5, 4, and 2) that last participates in the program on day 14.

In this 14-day program, 97% (108/111) of the users 101 completed 10 or more AM sessions. And, 71% (79/111) of the users 101 completed 14 AM sessions. The technical innovations disclosed herein (e.g., including the computing device 100) are responsible generally for such positive engagement rates.

FIG. 15B illustrates completion rates of the users in the 14-day program. The completion rates illustrated relate to the users' interactions in the mornings (AM) of the 14-day period. The users engage in the 14-day program via, inter alia, new-content-interaction modules 140 that activate in the mornings. The chart 1550 includes an axis 1560 and an axis 1570. The axis 1560 represents the days in the 14-day period. For example, a value of 1 represents day 1 of the 14-day period. The axis 1570 represents the completion rate/engagement rate on each day of the 14-day period. The completion rate/engagement rate represents the percentage of the 111 users 101 that completes the interaction in the mornings. In this 14-day program, over 90% of the users 101 completed the interaction in the morning on each day of the 14-day period. The technical innovations disclosed herein (e.g., including the computing device 100) are responsible generally for such positive completion rates.

As described herein, current smokers fall within a wide spectrum of TTM stages ranging from precontemplation (e.g., not interested in quitting smoking in next 6 months); to contemplation (e.g., interested in quitting smoking in next 6 months but not next 30 days); to preparation (e.g., interested in quitting smoking in next 30 days). An action stage may follow the preparation stage. The action stage represents a stage where a past smoker has quit smoking in the past 6 months. A maintenance stage may follow the action stage. The maintenance stage represents a stage where a past smoker quit smoking more than 6 months ago.

An example test of the effectiveness of a program implementing the computing device 100 may include the 111 users 101 (intervention participants) and 187 control participants. The control participants are participants that do not interact with the 14-day program implementation for smoking cessation via the computing device 100. The 111 intervention participants and 187 control participants are current smokers that were in precontemplation or contemplation stages before the example test. The test may indicate whether such a program is more likely to encourage users to transition from precontemplation or contemplation stages to preparation or action stages. In this example test, by day 15 (e.g., one day after the 14-day program concludes), 31% of the intervention participants had transitioned into the preparation stage and only 10% of the control participants have made the same transition. By day 45, 63% of the intervention participants had transitioned to the preparation stage (40%) or the action stage (23%). On the other hand, by day 45, only 19% of the control participants had transitioned to the preparation stage and only 3% had transitioned to the action stage (which amount to a total of 22%).

As illustrated by this example test, the 14-day program implementation for smoking cessation (e.g., a program implementing the computing device 100 described herein) is dramatically more effective at moving current smokers along the stages of change continuum and transitioning them to quit smoking. Even without offering a specific smoking cessation program at the conclusion of the 14-day period, by day 45, the current smokers had been nearly eight times more likely to have quit smoking (3% vs 23%).

In this example test, motivation, confidence, and readiness for a quit attempt have also improved. Before the test, for the control participants, their average ratings (e.g., on a scale of 1-10) for motivation, confidence, and readiness were 6.52, 5.62, and 6.16, respectively. For the intervention participants, their average ratings for motivation, confidence, and readiness were 6.84, 5.99, and 6.68, respectively. On day 14, for the control participants, their average ratings for motivation, confidence, and readiness were 6.49, 5.80, and 6.12, respectively. For the intervention participants their average ratings for motivation, confidence, and readiness were 7.81, 6.94, and 7.27, respectively. On day 45, for the control participants, their average ratings for motivation, confidence, and readiness were 6.12, 5.68, and 5.95, respectively. For the intervention participants, their average ratings for motivation, confidence, and readiness were 7.33, 6.79, and 6.82, respectively.

Engagement/completion rates are high, stage transition is dramatic, and motivation, confidence, and readiness are strong. The devices and technical methods disclosed herein may represent a striking improvement in the operation and effectiveness of smoking cessation devices. And this technical step forward in the device operation may result in better health outcomes for the users.

The invention claimed is:

1. A computing device for improving preparedness for a quit smoking attempt via a plurality of chronologically scheduled content-interaction modules, the computing device comprising:
a processor configured to:
execute a first content-interaction module associated with a user, wherein
the first content-interaction module transitions from an inactive state to an active state at a first start time on a first scheduled date, the first start time on the first scheduled date being associated with the first content-interaction module, the first content-interaction module being configured to present a user-activity content in the active state, the first content-interaction module being associated with one or more user actions related to a behavior change, and
the first content-interaction module transitions from the active state to the inactive state at the first end time on the first scheduled date, the first end time on the first scheduled date being associated with the first content-interaction module, the first content-interaction module being configured to restrict access to the user-activity content in the inactive state;
execute a second content-interaction module associated with the user having a corresponding second start time on a second schedule date, the second scheduled date being after the first schedule date associated with the first content-interaction module, the second content-interaction module comprising a follow-up content-interaction module, the follow-up content-interaction module being associated with the one or more user actions related to the behavior change; and
execute an enforcement module associated with the first content-interaction module when the user attempts to access the first content-interaction module between the first end time on the first scheduled date and the second start time on the second scheduled date and the first content-interaction module was not accessed between the first start time on the first scheduled date and the first end time on the first scheduled date, wherein the enforcement module prevents access to the first content-interaction module based on the first content-interaction module not being accessed between the first start time on the first scheduled date and the first end time on the first scheduled date, and wherein the enforcement module indicates that the first content-interaction module is no longer available and that the second content-interaction module will become available on the second scheduled date, and wherein the enforcement module enforces one or more rules associated with accessing any of the first content-interaction module or the second content-interaction module.

2. The computing device for improving preparedness for a quit smoking attempt via a plurality of chronologically scheduled content-interaction modules of claim 1, wherein the first start time of the first content-interaction module is a same time of day as the second start time of the second content-interaction module.

3. The computing device for improving preparedness for a quit smoking attempt via a plurality of chronologically scheduled content-interaction modules of claim 1, wherein the first scheduled date of the first content-interaction module and the second scheduled date of the second content-interaction module are two consecutive days.

4. The computing device for improving preparedness for a quit smoking attempt via a plurality of chronologically scheduled content-interaction modules of claim 1, wherein the first content-interaction module comprises a first new-content-interaction module and a first follow-up-content-interaction module.

5. The computing device for improving preparedness for a quit smoking attempt via a plurality of chronologically scheduled content-interaction modules of claim 1,
wherein the first content-interaction module comprises a first new-content-interaction module and a first follow-up-content-interaction module, the first new-content-interaction module being associated with a third start time on the first scheduled date and a third end time on the first scheduled date, and the first follow-up-interaction module being associated with a fourth start time on the first scheduled date and a fourth end time on the first scheduled date; and
wherein the first start time of the first content-interaction module is configured to be the same as the third start time of the first new-content-interaction module and the first end time of the first content-interaction module is configured to be the same as the fourth end time of the first follow-up-content-interaction module.

6. The computing device for improving preparedness for a quit smoking attempt via a plurality of chronologically scheduled content-interaction modules of claim 1,
the first content-interaction module comprises a first new-content-interaction module and a first follow-up-content-interaction module, the first new-content-interaction module being associated with a third start time on the first scheduled date and a third end time on the first scheduled date, and the first follow-up-interaction module being associated with a fourth start time on the first scheduled date and a fourth end time on the first scheduled date;

the first start time of the first content-interaction module is configured to be the same as the third start time of the first new-content-interaction module and the first end time of the first content-interaction module is configured to be the same as the fourth end time of the first follow-up-content-interaction module; and the processor is further configured to execute the enforcement module when the user attempts to access the first new-content-interaction module between the third end time of the first new-content-interaction module and the first end time of first content-interaction module, and the user missed accessing the first new content-interaction module between the third start time and the third end time, wherein the enforcement module indicates that the first content-interaction module is no longer available and that the second content-interaction module will become available on the second scheduled date.

7. The computing device for improving preparedness for a quit smoking attempt via a plurality of chronologically scheduled content-interaction modules of claim 1, the processor is further configured to:

execute a notification module, the notification module is configured to send an alert notification message to the user alerting the user to access the first content-interaction module at a predefined time before the first end time of the first content-interaction module, wherein the predefined time is one of: the first start time of the first content-interaction module, or a time after the first start time of the first content-interaction module.

8. The computing device for improving preparedness for a quit smoking attempt via a plurality of chronologically scheduled content-interaction modules of claim 1, the processor is further configured to:

execute a notification module, the notification module is configured to send a reminder notification message to the user reminding the user to access the first content-interaction module at a predefined time before the first end time of the first content-interaction module on a condition that the user missed accessing the first content-interaction module between the first start time of the first content-interaction module and the predefined time.

9. A computer-implemented method for improving preparedness for a quit smoking attempt via a plurality of chronologically scheduled content interactions, the method comprising:

presenting a first user-activity content between a first start time on a first scheduled date and a first end time on the first scheduled date, the first user-activity content being associated with one or more user actions related to a behavior change;

restricting access to the first user-activity content at the first end time on the first scheduled date;

presenting a second user-activity content between a second start time on a second scheduled date and a second end time on the second scheduled date, the second scheduled date being after the first scheduled date, the second user-activity content comprising follow-up content, the follow-up content being associated with the one or more user actions related to the behavior change;

detecting the user attempting to access the first user-activity content between the first end time on the first scheduled date and the second start time on the second scheduled date; and in response to the detection, indicating that the first user-activity is no longer available on the condition that the first user-activity was not accessed between the first start time on the first scheduled date and the first end time on the first scheduled date, wherein the indication prevents access to the first user-activity content based on the first user-activity content not being accessed between the first start time on the first scheduled date and the first end time on the first scheduled date, and wherein the indication is associated with enforcing one or more rules that are associated with accessing any of the first user-activity content or the second user-activity content.

10. The computer-implemented method for improving preparedness for a quit smoking attempt via a plurality of chronologically scheduled content interactions of claim 9, further comprising:

presenting a first user-activity content between a first start time on a first scheduled date and a first end time on the first scheduled date further comprising:

presenting the first user-activity content between a third start time on the first scheduled date and a third end time on the first scheduled date, and between a fourth start time on the first scheduled date and a fourth end time on the first scheduled date, wherein the third start time on the first scheduled date is the same as the first start time on the first scheduled date, the fourth end time on the first scheduled date is the same as the first end time on the first scheduled date.

11. The computer-implemented method for improving preparedness for a quit smoking attempt via a plurality of chronologically scheduled content interactions of claim 10, further comprising:

detecting the user attempting to access the first user-activity content between the third end time of the first schedule date and the fourth end time on the first scheduled date; and in response to the detection, indicating that the first content-interaction module is no longer available and that the second content-interaction module will become available on the second scheduled date.

12. The computer-implemented method for improving preparedness for a quit smoking attempt via a plurality of chronologically scheduled content interactions of claim 9, further comprising:

sending an alert notification message to the user alerting the user to access the first content-interaction module at a predefined time before the first end time of the first content-interaction module, wherein the predefined time is one of: the first start time of the first content-interaction module, or a time after the first start time of the first content-interaction module.

13. The computer-implemented method for improving preparedness for a quit smoking attempt via a plurality of chronologically scheduled content interactions of claim 9, further comprising:

sending a reminder notification message to the user reminding the user to access the first content-interaction module at a predefined time before the first end time of the first content-interaction module on a condition that the user missed accessing the first content-interaction module between the first start time of the first content-interaction module and the predefined time.

14. A computing device for changing health behavior via a plurality of chronologically scheduled content-interaction modules, the computing device comprising:
a processor configured to:
execute an enforcement module associated with a first content-interaction module when the user attempts to access the first content-interaction module between a first end time on a first scheduled date and a second start time on the second scheduled date and the first content-interaction module was not accessed between a first start time on the first scheduled date and a first end time on the first scheduled date, wherein the enforcement module prevents access to the first content-interaction module based on the first content-interaction module not being accessed between the first start time on the first scheduled date and the first end time on the first scheduled date, and wherein the enforcement module indicates that the first content-interaction module is no longer available and that a second content-interaction module will become available on the second scheduled date, and wherein the enforcement module enforces one or more rules associated with accessing any of the first content-interaction module or the second content-interaction module.

15. The computing device of claim 14, wherein the first content-interaction module presents smoking cessation information, comprising an activity regarding any of reasons for smoking, the dependence on nicotine, craving satisfaction, smoking triggers, distraction techniques, medical warning signs, concerns about smoking, reasons for quitting smoking, core values, temptations, benefits of seeking help from others, or visualizing destroying a cigarette.

16. The computing device of claim 14, wherein the first content module presents healthy pregnancy information, comprising an activity regarding sleep, nutrition, mood, or movement.

17. The computing device of claim 14, wherein the first content module presents healthy eating information, comprising an activity regarding core values' relation with eating, food choices, mindful eating, reason for eating, self-control over eating, or healthier coping with stress.

18. The computing device of claim 14, wherein the first content-interaction module comprises an activity and a psychological reward associated with the activity.

19. The computing device of claim 14, wherein the first content-interaction module selects an activity from a plurality of stored activities based on user-analytics, and wherein the first content-interaction module selects the activity based on a history of greater user interaction than an unselected activity.

20. The computing device of claim 14, wherein the enforcement module comprises a user message indicating that the user's non-compliance with the access rules result in the user losing out on experiencing an activity of the first content-interaction module.

* * * * *